US012293827B2

(12) United States Patent
Martin et al.

(10) Patent No.: US 12,293,827 B2
(45) Date of Patent: May 6, 2025

(54) INFERRING A CONDITION OF A MEDICAL ANALYZER

(71) Applicant: Roche Diagnostics Operations, Inc., Indianapolis, IN (US)

(72) Inventors: Stephen Martin, Zug (CH); Jakub Winiarz, Zug (CH); Alexandra Paun, Zurich (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 979 days.

(21) Appl. No.: 17/365,464

(22) Filed: Jul. 1, 2021

(65) Prior Publication Data
US 2022/0020489 A1 Jan. 20, 2022

(30) Foreign Application Priority Data
Jul. 14, 2020 (EP) ..................................... 20185739

(51) Int. Cl.
*G16H 40/67* (2018.01)
*G16H 10/40* (2018.01)
(52) U.S. Cl.
CPC ............. *G16H 40/67* (2018.01); *G16H 10/40* (2018.01)
(58) Field of Classification Search
CPC .............................. G16H 10/40; G16H 40/67
See application file for complete search history.

(56) References Cited

U.S. PATENT DOCUMENTS

| 5,924,074 A * | 7/1999 | Evans ................... G16H 20/10 |
| | | 707/999.001 |
| 7,243,270 B2 | 7/2007 | Taniguchi et al. |
| 8,595,553 B2 | 11/2013 | Goertler et al. |
| 10,049,346 B2 | 8/2018 | Jensen et al. |
| 2004/0138920 A1 | 7/2004 | Sawanaga et al. |
| 2007/0162190 A1 | 7/2007 | Choubey |
| 2011/0121969 A1 | 5/2011 | Mercer et al. |

(Continued)

FOREIGN PATENT DOCUMENTS

| JP | 2005-110794 A | 4/2005 |
| JP | 2006-149873 A | 6/2006 |

(Continued)

OTHER PUBLICATIONS

European Search Report issued Dec. 11, 2020, in Application No. 20185739.8, 2 pp.

*Primary Examiner* — Jigar P Patel
(74) *Attorney, Agent, or Firm* — Lee & Hayes, P.C.

(57) ABSTRACT

A computer-implemented method for inferring a condition of at least one analytical device based on at least one automatic notification received over a network from the analytical device is disclosed. The method comprises receiving, at a data processing agent, at least one automatic notification from at least one analytical device, processing, at the data processing agent, the at least one automatic notification, to thus identify one or more characteristics of the at least one automatic notification from the at least one analytical device, inferring, at the data processing agent, the condition of the at least one analytical device, by applying the one or more identified characteristics to a model; and generating, at the data processing agent, a notification reporting the inferred condition of the analytical device.

14 Claims, 10 Drawing Sheets

(56) References Cited

U.S. PATENT DOCUMENTS

| | | | |
|---|---|---|---|
| 2015/0227838 A1 | 8/2015 | Wang et al. | |
| 2020/0160954 A1* | 5/2020 | Lyman | G06F 3/0484 |
| 2022/0005565 A1* | 1/2022 | Lyman | G16H 15/00 |

FOREIGN PATENT DOCUMENTS

| | | |
|---|---|---|
| JP | 2019-008675 A | 1/2019 |
| WO | 2018/091492 A1 | 5/2018 |

\* cited by examiner

INFERRING A CONDITION OF A MEDICAL ANALYZER

CROSS-REFERENCE TO RELATED APPLICATIONS

This application is a continuation of EP 20185739.8, filed Jul. 14, 2020, which is hereby incorporated by reference.

BACKGROUND

The present disclosure generally relates to a computer-implemented method for inferring a condition of at least one analytical device, and an associated apparatus, a networked system, a computer program element and a computer readable medium.

In clinical care environments, an analytical device can be used at, or near to, the point of care. Such analytical devices are designated as "Point of Care (POC) testing devices." The analytical devices can communicate a variety of automatic notifications containing information about the technical status of the testing devices with a central server, for example.

POC devices such as, for example, analytical devices, send a large number of automated notifications denoting, for example, events, analysis results, or other analyzer status information to a POC IT data management system.

A typical POC device generates a significant number of device messages. Consequently, the coherent monitoring of information concerning the status of a large number of POC devices can be challenging. Therefore, such POC devices and their management systems can be further improved.

SUMMARY

According to the present disclosure, an apparatus and computer-implemented method for inferring a condition of at least one analytical device based on at least one automatic notification received over a network from the analytical device are presented. The method can comprise receiving, at a data processing agent, at least one automatic notification from at least one analytical device, processing, at the data processing agent, the at least one automatic notification, to thus identify one or more characteristics of the analytical device based on the at least one automatic notification, from the at least one analytical device, inferring, at the data processing agent, the condition of the at least one analytical device, by applying the one or more identified characteristics to a model, receiving, at the data processing agent, at least one item of annotation data via the network, associating, at the data processing agent, the one or more items of annotation data with one or more of the at least one automatic notifications, inferring the condition of the at least one analytical device based, additionally, on the association between the at least one item of annotation data with the at least one automatic notifications, and generating, at the data processing agent, a notification reporting the inferred condition of the analytical device.

Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
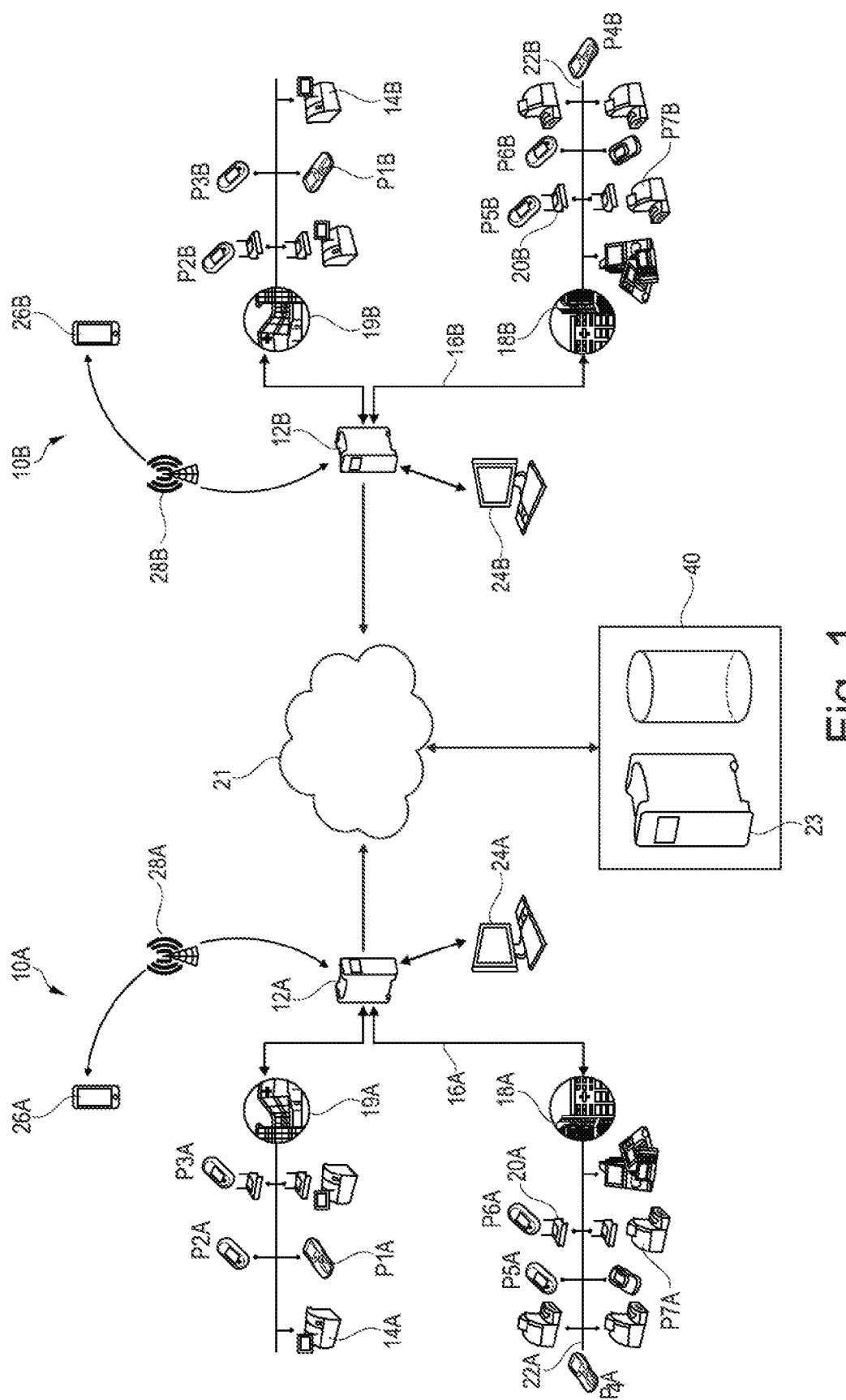
FIG. 1 illustrates schematically a networked system for analytical device management according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A computer-implemented method for inferring a condition of at least one analytical device based on at least one automatic notification received over a network from the analytical device is provided. The method can comprise receiving, at a data processing agent, at least one automatic notification from at least one analytical device; processing, at the data processing agent, the at least one automatic notification, to thus identify one or more characteristics of the analytical device based on the at least one automatic notification, from the at least one analytical device; inferring, at the data processing agent, the condition of the at least one analytical device, by applying the one or more identified characteristics to a model; and generating, at the data processing agent, a notification reporting the inferred condition of the analytical device.

An effect of this can be that the maintenance condition of one or more analytical devices may be accurately tracked. Information gathered from a first network of analytical devices may be applied to further networks of analytical devices.

Furthermore, a large number of automatic notifications may be processed to identify trends or patterns in the notifications, which enable the timely prediction of maintenance problems. Alternatively, a database of historical notifications may be post-processed to discern trends or to learn about patterns in the data that are difficult to identify.

The future maintenance condition of one or more analytical devices may be predicted or inferred at a particular point in time.

A maintenance schedule may be generated, or updated, to reflect the importance or urgency of changes to the physical state of one or more analytical devices.

A user of one or more analytical devices may be advised, via a graphical user interface (GUI) or other displays, about action to take to resolve an inferred condition of an analytical device.

An apparatus configured to host a data processing agent for inferring a condition of at least one analytical device based on at least one automatic notification received over a network from the analytical device is provided. The apparatus can comprise a communications interface and a processor coupled to the communications interface.

The communications interface can be configured to receive at least one automatic notification from at least one analytical device.

The processor can be configured to process at least one automatic notification, to thus identify one or more characteristics of the analytical device based on the at least one automatic notification from the at least one analytical device.

The processor can be configured to infer the condition of the at least one analytical device, by applying the one or more identified characteristics to a model.

The processor can be configured to generate a notification reporting the inferred condition of the analytical device.

A system for analytical device management is provided. The system can comprise at least one analytical device and an apparatus configured to host a data processing agent for processing data from the above apparatus, which can be configured to perform the above method.

The system can further comprise a computing apparatus comprising a user interface, and a network configured to communicatively connect the at least one analytical device, the computing device, and the apparatus configured to host the data processing agent.

The at least one analytical device can be configured to generate a plurality of notifications and the communication network can be configured to communicate the plurality of notifications to the data processing agent hosted on the apparatus.

In an embodiment, the at least one analytical device can be configured to analyze biological samples from a patient.

In an embodiment, the at least one analytical device can be configured to analyze biological samples to identify a biomarker of a medical condition.

A computer program element comprising computer-readable instructions for controlling the above apparatus which, when being executed by a processor of the apparatus, can be configured to perform the above method.

A computer readable medium or signal having stored, or encoded thereon, the above computer program.

A computer-implemented method for generating a model for inferring the state of an analytical device based on a plurality of automatic notifications received from a network is provided. The method can comprise receiving a plurality of automatic notifications from one or more analytical devices in one or more networks, at least one subset of the plurality of automatic notifications is associated with at least one condition of at least one of the one or more analytical devices and training a model using the plurality of automatic notifications as training data to generate the model, wherein the model provides a relationship between the plurality of received automatic notifications and the at least one condition of at least one of the one or more analytical devices.

A computer readable data structure comprising a trained model obtained is provided.

As used herein, the terms "comprises", "comprising", "includes", "including", "has", "having", or any other variation thereof, are intended to cover a non-exclusive inclusion.

The terms "patient sample" and "biological sample" can refer to material(s) that may potentially contain an analyte of interest. The patient sample can be derived from any biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. The patient sample can be pretreated prior to use, such as preparing plasma from blood, diluting viscous fluids, lysis, or the like. Methods of treatment can involve filtration, distillation, concentration, inactivation of interfering components, and the addition of reagents. A patient sample may be used directly as obtained from the source or used following a pretreatment to modify the character of the sample. In some embodiments, an initially solid or semisolid biological material can be rendered liquid by dissolving or suspending it with a suitable liquid medium. In some embodiments, the sample can be suspected to contain a certain antigen or nucleic acid.

The term "analytical device" as used herein can encompass any apparatus for obtaining measurement values relating to a medical condition of a patient. In one example, the measurement values may be provided by obtaining a patient sample, and using an analytical device to automatically, or semi-automatically process the patient sample. The analytical device may detect the presence of analytes in the processed sample, from which an assessment of the medical condition of a patient may be made. It is not essential that the analytical device forms the assessment of the medical condition of a patient—for example, a summary of the analytes detected by the analytical device can be provided to a medical professional for further consideration. In another example, an "analytical device" may obtain and process digital data that represents a medical condition of a patient. The digital data may be received as measurement values from other analytical devices, and/or as image, video, or sound data.

In one example, the analytical device may be an automated analyzer of biological (medical) samples obtained from a patient providing a measurement value relating to a medical condition of a patient. For example, an analytical device may measure light absorption, fluorescence, electrical potential or other physical or chemical characteristics of the reaction to provide the measurement value. Often such patient samples can be treated before analytical testing is done. Blood sampled from a patient is e.g. centrifuged to obtain serum or treated with anti-coagulants to obtain plasma.

Analytical testing by an analytical device can have, as an example, the goal of determining the presence and/or concentration of an analyte in a patient sample. The term "analyte" can be a general term for substances for which information about presence and/or concentration is intended. Examples of analytes are e.g., glucose, coagulation parameters, endogenous proteins (e.g., proteins released from the heart muscle), metabolites, nucleic acids and so on.

Analytical testing by an analytical device configured to analyze patient samples can have, as an example, the goal of determining the presence and/or concentration of an analyte in a patient sample. However, obtaining and processing digital data obtained by a camera sensor of a chemical reaction, or an image of the skin of a patient, for example, can be another example of analytical testing.

It may not be essential that an "analytical device" automatically perform all steps required to obtain data about the medical condition of a patient. For example, some analytical devices may require a POC operator to pipette reagent into a sample in an ampoule or mount a slide prior to the performance of a test. In other cases, the "analytical device" may automatically perform all steps of a sample analysis without operator intervention. In other cases, the "analytical device" may prompt a user to intervene manually at a stage of the analysis.

Alternatively, the analytical device can be a handheld or mobile device comprising sensors configured to acquire measurement values from a patient.

An "analytical device" may comprise a portable appliance that can be communicatively connected to a smartphone, tablet PC, smart watch, or other computing device via a USB (™), WiFi (™), or Bluetooth (™) connection, for example. Such a portable appliance may be configured to perform analytical testing by analyzing data obtained from one or a combination of sensors.

A measurement value may comprise data collected from, for example, the sensors of a smartphone. By way of example only, a measurement value may be data obtained by a smartphone accelerometer that can characterize a degree of patient tremor. A measurement value may be a photograph of a dermatological condition obtained using a smartphone camera. A measurement value may be a sound recording obtained using a smartphone microphone. A measurement value may be a video obtained using a smartphone for the purposes of assessing patient gait, for example. In this way, standard features of smartphones, tablet PCs, or other computing devices may perform the function of an analytical device. An application executed on a smartphone, or other computing device, may be capable of obtaining such data and communicating it to a data processing agent. A wider suite of measurement values may be obtained via an extension device communicatively coupled to the smartphone. For example, an extension device can comprise a digital thermometer.

The term "patient health parameter" as used herein can encompass any aspect of a patient's physiology that is measurable or indicated by an analysis of a patient sample for one or more analyte, or by analysis of data obtained from one or a combination of sensors.

An "analytical device" may be configured so as to be usable in the vicinity of a patient ward, in which case it is often referred to as a "Point of Care (POC) device". However, the techniques discussed herein are not limited to POC devices and may be applied to many types of laboratory analysis systems that generate message data.

The term "Point of Care (POC)" or "Point of Care environment" as used herein can be defined to mean a location on or near a site of patient care where medical or medically related services such as medical testing and/or treatment are provided, including but not limited to hospitals, emergency departments, intensive care units, primary care setting, medical centers, patient homes, a physician's office, a pharmacy or a site of an emergency.

In the field of bedside testing or point of care testing, the testing can be typically performed by nurses, medical staff, or doctors but also pharmacists who are collectively called "operator(s)" herein. However, anyone who possesses the required certification may be an operator. A point of care coordinator (POCC) may be at the same time an operator of POC analyzer(s) and an operator of POC analyzer(s) may be at the same time a point of care coordinator (POCC) and thus user of portable computing device(s).

The term "point of care testing" POCT as used herein can encompass analysis of one or more items of data provided by an analytical device as defined above, to obtain information about the medical condition of a patient. POCT is often accomplished through the use of transportable, portable, and handheld instruments, but small bench analyzers or fixed equipment can also be used when a handheld device is not available—the goal being to collect a patient sample and obtain analytical data in a (relatively) short period of time at or (relatively) near the location of the patient.

In an example, POCT can be performed using various analytical devices (i.e., POC analyzers) such as (but not limited to) analyzers for glucose, coagulation, blood gas, urinalysis, cardiac and molecular testing. Results may be viewed directly on the POC analyzer(s) or may be sent to the POCT system and displayed in a Laboratory Information System (LIS) with central lab results, or alongside imaging results in a Hospital Information System (HIS).

Therefore, an analytical device may be used in a point of care environment, to perform tests such as (but not limited to) blood glucose testing, coagulation testing, blood gas and electrolytes analysis, urinalysis, cardiac markers analysis, hemoglobin diagnostics, infectious disease testing, cholesterol screening or nucleic acid testing (NAT). Results may be viewed directly on a Point of Care analyzer(s) or may be sent to a Point of Care testing system and displayed in a Laboratory Information System (LIS) with central lab results, or alongside imaging results in a Hospital Information System (HIS). The term "patient health parameter" may optionally encompass digital data such as an image or video that can provide information about any aspect of a patient's physiology.

In an example, POCT can be performed by obtaining digital data such as a photograph of a portion of the skin of a patient, a video of the patient walking, or a sound sample of the patient making a sound.

In an example, POCT can be performed using a "portable computing device" that can encompass any electronic appliance that can be moved easily from one location to another, in particular any handheld battery powered mobile appliance, including but not limited to a cellular telephone, a satellite telephone, a pager, a personal digital assistant ("PDA"), a smartphone, a navigation device, a smart book or reader, a combination of the aforementioned devices, a tablet computer or a laptop computer.

The term "point of care device management system" (POC-DMS) as used herein can denote a data processor configured to communicate with and manage one or more POC devices via a computer network to enable a POC coordinator to manage the POC devices, or to enable maintenance personnel to monitor the equipment. Optionally, the POC-DMS can be a terminal computer connected to the same network that the POC devices are connected to. Optionally, the POC-DMS may be provided as a server, virtual machine or a virtualized server hosted remotely to the network that the POC devices are connected to, enabling remote management of the POC devices. It may not be essential that the POC devices (i.e., analytical devices) be connected to the same subnet, or network branch, for example, as the POC-DMS.

An analytical device may generate "automatic notifications". Some automatic notifications can be data messages containing assay results of tests performed on the analytical device. Other automatic notifications can contain feedback about the condition of the analytical device, such as: hardware heartbeats, specific hardware faults such as messages reporting motor overheating, battery condition, or a lid jam, networking information (such as LDAP or DHCP lookup messages), reagent information, temperature information, incremental counts of the number of assays performed, battery levels, software or firmware update requests, user logon information, audit log messages, security certificate messages, memory capacity information, and the like. A skilled person can appreciate many different types of analytical devices can generate a wide variety of analytical device notifications.

The term "context" in relation to an analytical device can refer to a collection of observations that may be made by or about an analytical device in a situation, location, and/or in operation conditions that can distinguish between different uses of the analyzer. "Contexts" can represent categorizable technical concepts concerning the use environment of an analytical device. The presence of a context may be detected, or iterated from, based on input stimuli detected by sensors of the analytical device of medical samples, or by the fusion of contextual information such as network address of an analytical device, at a given time.

Furthermore, example categories of technical concepts that can represent contexts may be use of an analytical device in a "teaching lab", "maintenance department", and "accident and emergency department".

The technical input stimuli derived from an analytical device sensor may be used as inputs to a range of logical rules, or a model, for example a model obtained by machine learning techniques. The rules can enable an inference of which context the analytical device is operating in. A simple example of a context change may be taking an analytical device from a room with an acceptable temperature into a room that is too cold for an assay to be performed reliably. The context change may be inferred because an electronic thermometer included in the analytical device may report the temperature of the analytical device over time. Alternatively, the movement of the analytical device to the "maintenance department" may result in the broadcast, from the analytical device, of a plurality of unusual messages relating to the dismantling of the analytical device, such as hardware interlock signals.

The fusion of data from more than one input stimulus can enable a more accurate determination of the context. For example, by only monitoring the temperature of the analytical device, it may not be possible to determine whether or not the analytical device has moved room, or whether the temperature of same room has changed. However, information from external databases, such as a network address database or a wireless network registry may enable more accurate tracking of an analytical device around rooms in a hospital. The offline fusion of information from a user database with sensor data from the analytical device may enable the detection of the use history of the analytical device.

The term "message type" can refer to the fact that for each analytical device, one or more automatic notifications from a finite set of automatic notifications can be transmitted from the analytical device based on the status of the analytical device sending the automatic notification. The range of automatic notifications (messages) may be defined in a messaging specification.

The phrase "identify one or more characteristics of the at least one automatic notification", for example, may imply a subsampling of the total set of automatic notifications to generate a suitable input for a model that infers the condition of an analytical device. For example, when inferring the condition of a battery, it may not be necessary to train the model, or to apply the model, based on automatic notifications referring to the software version of an analytical device, for example. The identification of one or more characteristics can thus be a reduction in the information content of the stream of input automatic notifications.

The term "condition" of an analytical device can refer to a status of a hardware or software element of the analytical device that is unique to that analyzer. In one option, the "condition" of an analytical device may be selected from one of several conditions, such as "good condition", "average condition", or "requires maintenance in the next week", or "device out of use until maintained". Alternatively, the "condition" of an analytical device may be a continuous number defined based on a scoring system. A non-urgent characteristic in the automatic notifications from an analytical device such as "photometer clean" may be assigned a low priority score, whereas an urgent characteristic in the automatic notifications from an analytical device such as "photometer unresponsive" may be assigned a high priority score.

The "condition" of an analytical device may be a function of how much the analyzer has been used, the training level of personnel using analyzer, the type of analyzer, the context in which analyzer is used, and the like. The "condition" can be, as an example, a composite of a wide range of factors such as (i) battery status, (ii) number of assays performed, (iii) quality control results, (iv) software version, (v) photometer condition, (vi) door mechanism condition, and the like. Accordingly, the condition of an analytical device may be inferred based on a subsampled selection of the automatic notifications. A skilled person can appreciate that the range and definition of conditions detectable, to some extent, depend on the range of automatic notifications available for processing, and on the priorities of the end user who defines a maintenance schedule of the analytical device.

The term "communication network" as used herein can encompass any type of wired or wireless network, including but not limited to a WIFI, GSM, UMTS or other wireless digital network or a wired network, such as Ethernet or the like. For example, the communication network may include a combination of wired and wireless networks. Automatic notifications may be transmitted from an analytical device over the communication network.

The term "server" can encompass any physical machine or virtual machine having a physical or virtual processor, capable of accepting requests from and giving responses accordingly. It can be clear to a person of ordinary skill in the art of computer programming that the term machine may refer to a physical hardware itself, or to a virtual machine such as a JAVA Virtual Machine (JVM), or even to separate virtual machines running different Operating Systems on the same physical machine and sharing that machine's computing resources. Servers can run on any computer including dedicated computers, which individually are also often referred to as "the server" or shared resources such as virtual servers. In many cases, a computer can provide several services and have several servers running. Therefore, the term server can encompass any computerized device that can share a resource to one or more client processes. The server can receive, process, and transmit automatic notifications.

The term "server interface" can encompass any hardware-, firmware- and/or software-based module operable to execute program logic to allow communication with an external entity (such as a server or another interface).

The term "data processing agent" can refer to a computer implemented software module executing on one or more computing devices, such as a server, that can be able to receive automatic notifications from a point of care device, and optionally annotation data from a user or operator. In an example, the data processing agent can infer a characteristic of an analyzer device based on the received automatic notifications. In an example, the data processing agent may associate the automatic notifications and the annotation data. The "data processing agent" may be implemented on a single server, or between multiple servers, and/or on an internet-based "cloud" processing service such as Amazon AWS (™) or Microsoft Azure (™). The "data processing agent", or a portion of it, may be hosted on a virtual machine. The data processing agent can receive, process, and transmit automatic notifications.

The term "user interface" can encompass any suitable piece of software and/or hardware for interactions between an operator and a machine, including but not limited to a graphical user interface (GUI) for receiving as input a command from an operator and also to provide feedback and convey information thereto. In addition, a system/device may expose several user interfaces to serve different kinds of users/operators. The user interface may display automatic notifications. The user interface may display a maintenance report.

Point of Care (POC) analyzers (also known as analytical devices) can be commonly managed by a server, and in particular, a hardware management server, also called Point of Care Data Management System (POC-DMS). The POC-DMS can provide connectivity for the analytical devices, management of test results, operators, quality control and can track the maintenance regime of the analytical devices. For example, one POC-DMS can manage all analytical devices in a hospital, hospital department, or medical testing center.

Management of analytical device systems can be challenging—there can be dozens of sites, hundreds of analytical devices, and thousands of operators to manage to assure quality of testing. One challenge in managing a large POC device concerns tracking the maintenance status of tens, or hundreds, of analytical devices.

Analytical devices can send a large amount of data comprised of regular device messages, event messages, usage messages, system warning messages, and errors (analytical device data) to a system for analytical device management (POC-DMS). The reporting of analytical device maintenance requirements can be further improved.

Some maintenance can be performed in-place (such as battery replacement), whereas other maintenance can require the analytical device to be sent away to a maintenance center (such as mechanical repair). Typically, maintenance of analytical devices can be provided on a regular timetable, but selecting the time interval between maintenance can lead to inefficiently frequent maintenance of analytical devices that do not require maintenance, or a maintenance schedule that is too infrequent and does not determine possible faults of a given POC analyzer promptly enough.

Accurate assessment of analytical device maintenance requirements can enable spare parts to be ordered preemptively, for example. Accurate assessment of analytical device maintenance requirements can also improve analytical device availability ratios, and reduce the risk that a given analytical device may fail unexpectedly in use.

The pre-emptive conditions experienced by an analytical device that lead to a maintenance requirement can depend partially on the type of analytical device in question, its use history, and a degree of variation. These conditions can be detected by various pre-existing sensors in analytical devices.

In this context, determining an improved maintenance schedule or maintenance alarm may not be a problem of an exclusively administrative character—sensor feedback from one or more analytical devices can enable an improved and automatic assessment of a maintenance requirement, or even enable faults to be accurately and automatically pre-empted, based on the particular use context of an individual analytical device.

The present disclosure generally proposes to use automatic notifications received from one or more analytical devices to generate a notification reporting an inferred condition of the one or more analytical devices. In an example, automatic notifications from a first set of analytical devices can be used to train a model. The model can define a relationship between a received set of automatic notifications, and a condition of an analytical device that may be inferred from the received set of automatic notifications.

When trained, the model may be provided to a further network of analytical devices, so that similar patterns of automatic notifications received in the further network can be used to infer the condition of one or more analytical devices in the further network. Although the model may be trained using machine learning techniques (for example, supervised learning or unsupervised learning), this may not be essential.

A model can define a mapping between a set of input notifications and an inferred condition. Therefore, in a simpler case, the model can be provided as a predefined logical rule set provided by a manufacturer, for example, rather than as a trained model.

Alternatively, automatic notifications from a second set of analytical devices P1B-P7B in the second network 10B may be provided to a data processing agent 40 comprising a model trained using automatic notifications received from a first set of analytical devices P1B-P7B in the first network 10A.

FIG. 1 schematically illustrates a networked system 10 for analytical device management. The networked system 10 for analytical device management can comprise a first network 10A. The first network 10A may be divided into one or more Local Area Networks (LANs) or Wide Area Networks (WANs) corresponding to a first location 18A housing analytical devices, and a second location 19A housing analytical devices. For example, first location 18A may represent a local clinic, and second location 19A may represent a general hospital. The number of locations in the first network 10A of the networked system 10 may not be essential to the functioning of the system described.

The system can comprise one or more analytical devices (e.g., POC devices) P1A-P7A, optionally a portable computing device 26A (such as a smartphone), and a server 12A communicatively connected by a communication network 16. The server 12A may, in an example, host a data processing agent 23 according to the first aspect. In other examples, the data processing agent may be hosted by a cloud computing service distributed over a plurality of servers and computing devices. In particular, the communication network 21 can be configured to communicatively connect the one or more analytical devices P1A-P7A.

The communication network 21 may, for example, comprise one or more of a local area network (LAN) provided over, for example, an Ethernet network, a Wi-Fi network, and/or a wide area network (WAN) such as the Internet. The communications network may comprise a Mobile Telecommunications network such as a 3G, 4G, or 5G system 28, and/or a hospital PACS network.

Optionally, the communication network 16 may connect the server 12 directly to the analytical devices (e.g., POC devices) P1A to P7B (not illustrated).

Optionally, the communication network 21 can interface with an internal communications system 22A of a health facility 18A. The internal communications system 22A may be an intranet, for example.

A firewall, and other security measures known to a person skilled in the art, may be placed in between the internal communications system 22A and the communications network 21 to ensure security and confidentiality whilst still enabling the communication of automatic notifications. The analytical devices P1A-P7A may communicate with a data processing agent 23 hosted on a server 40, for example, by communicating via the internal communications system 22 and the communication network 16.

The analytical devices P1A-P7A can be provided and configured to analyze one or more patient samples in order to measure one or more patient health parameters.

The analyzers P1A-P7A can be located in the first location 18A (corresponding to a local clinic), for example. The fixed equipment 14 may be located in second location 19A (corresponding to a general hospital, for example).

In order to identify a particular analytical device P1A-P7A, each analytical device can be provided with an analyzer identifier code, in particular in the form of an identifier tag such as a barcode and/or an RFID tag or a serial number. Optionally, such identifiers may be associated with an entry in a database of the system for analytical device management.

The analyzers P1A-P7A can be, for example, configured to transmit automatic notifications (e.g., analytical device status data or event messages) from the analyzers to the server 12 over the communications network 16.

The networked system 10 for analytical device management can further comprise a Point of Care Data Management System (POC-DMS), hosted, for example, on server 12A. The purpose of the POC-DMS can be to monitor and control one or more analytical device P1A-P7A in a defined area, or network branch. For example, a POC administrator personnel can use the POC-DMS hosted on server 12A to track the condition of one or more of the analytical devices P1A-P7A, to monitor consumable usage, and a wide variety of other management activities.

The networked system 10 for analytical device management can also comprise a further network 10B. The further network 10B can represent a network of analytical devices run at a different hospital site, or in a different country, or hospital department as compared to the first network 10B. The description of the individual components provided above in respect of the network 10A can also apply to the illustrated components of the further network 10A for reasons of brevity. A skilled person can appreciate that a further network 10B may have a significantly different architecture to that illustrated.

In particular, the second POC-DMS 12B can also encounter problems of how to process and/or display a large number of analytical device message data output from the analytical devices P1B-P7B.

A large number of analytical devices P1A-P7A connected to a network 10A can generate thousands or tens of thousands of automatic notifications per hour, reflecting the internal condition of the analytical devices P1A-P7A.

Point of care devices (i.e., analytical devices P1A-P7A) can send regular device messages (automatic notifications) to a point-of-care data management system 12A. Those device messages can inform the user about events, usage, system warnings, and errors. Optionally, the device messages may be combined with using notes (annotations) that create a comprehensive audit trail of all events, or a substantial proportion of events, that have happened on a specific device. This can enable maintenance decisions to be taken based on the inferred condition of the analyzers.

Figure 2:
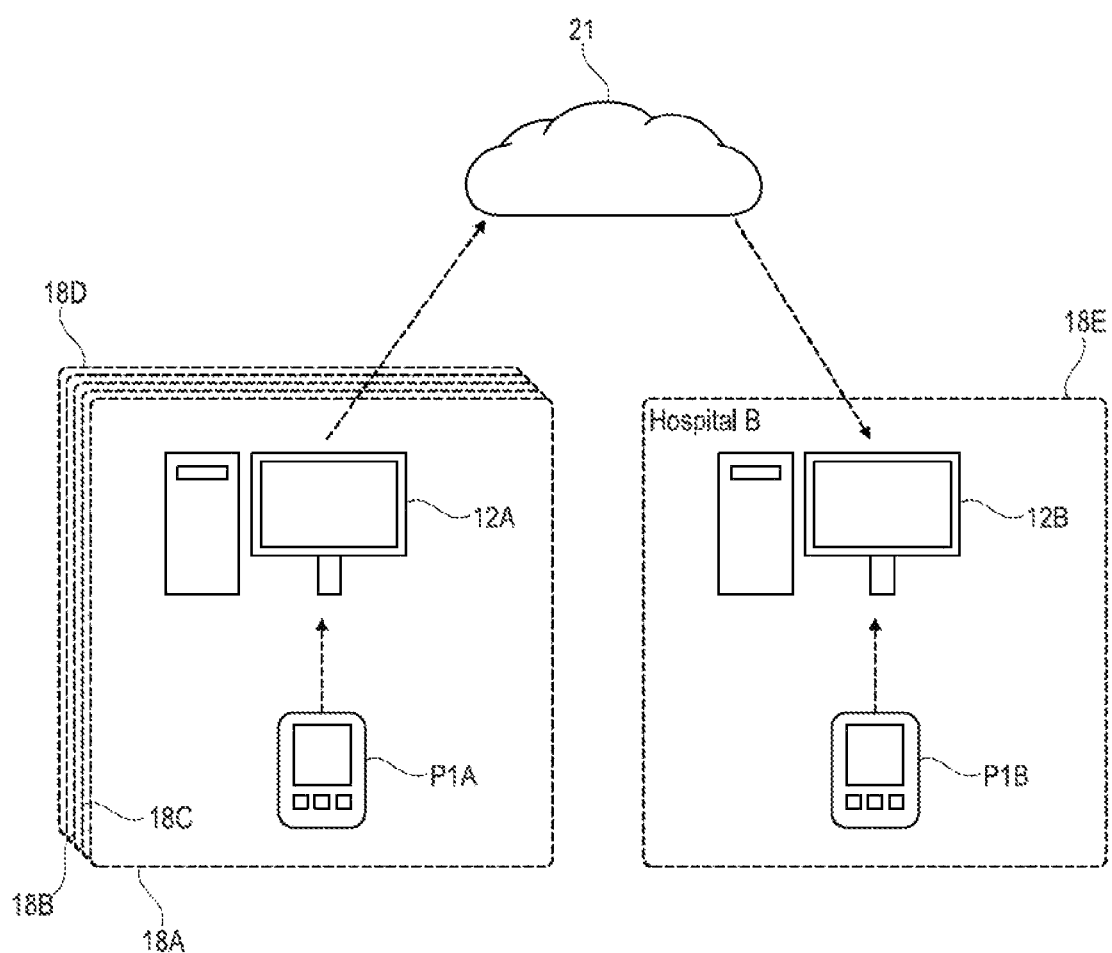
FIG. 2 illustrates schematically messaging flow in a system for analytical device management according to an embodiment of the present disclosure.

FIG. 2 schematically illustrates messaging flow in the system 10, 10B for analytical device management.

A first network 18A comprising an analytical device P1A (such as an analytical device) and a point-of-care device management system (POC-DMS) 12A can be connected to the POC-DMS 12A via communications link 21 such as the Internet. Optionally, further networks 18B, 18C, 18D . . . can be connected via communications link 21. Analytical devices such as P1A in the first network 18A can generate a large number of automatic notifications per hour.

A further network 18E that can also be communicatively coupled via network 21 may contain a similar selection of analytical devices (such as P1B).

In other words, the system of this specification can, for example, inform proactively, using generated notifications from analytical devices, about prospective possible analytical device failures and/or required maintenance activities for analytical devices. These generated notifications can be created based on identified patterns and chains of events that lead to device failure. Such patterns can be identified based on collected and analyzed device events and notes from across different hospitals and devices.

In an example, a number of hospitals 18A, 19A, 18B, 19B may use a certain type of analytical device P1A-P7A, P1B-P7B. For example, automatic notifications from P1A can be regularly sent to POC-DMS 12A, which can share them with a central analysis and storage system (data processing agent 40, for example).

If, for example, a sensor failure in analytical device P1A is identified, the user may, for example, attempt to reinstall the software of the analytical device P1A. However, because the fault is due to a sensor failure, the problem can persist. The analytical device P1A can then be marked as broken and returned to the manufacturer the sequence of events leading up to the return of the analytical device P1A can be stored in the data processing agent 40 and its associated databases for future analysis.

Other similar cases may appear in other hospitals, enabling the system to recognize a pattern that can lead to a sensor failure (for example, around 100 failed QC results in a row). The system may therefore proactively inform the user of a POC-DMS 12B in a further network, when the system recognizes the same pattern that can lead to the same failure in an analytical device P1B in the second network 10B.

Figure 3:
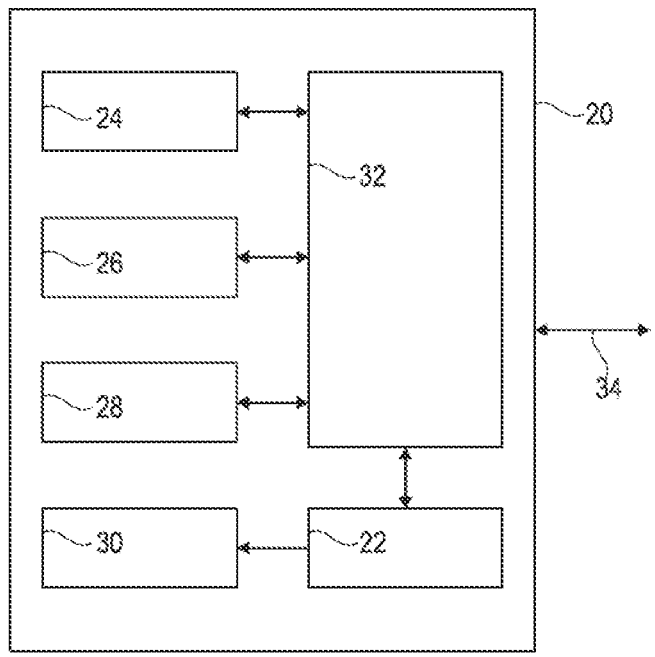
FIG. 3 illustrates schematically an example of an analytical device according to an embodiment of the present disclosure.

FIG. 3 schematically illustrates an example of an analytical device 20 (e.g., Point of Care (POC)).

The example of the analytical device 20 can comprise a power supply 22 configured to provide power to the analytical device 20. The power supply 22 may be, for example, a lithium ion battery enabling the analytical device 20 to be portable, or a mains power supply. The power supply 22 can provide electrical energy to the other elements of the analytical device 20. The other elements can comprise, for example: a sensor device 24, an electromechanical subassembly 26, a specimen processing section 28, and an analysis unit 30. A control and communication subsystem 32 can interface with the previously listed modules. A communications link 34 can enable data transfer to and from the analytical device 20.

The sensor device 24 may, for example, comprise a photometer for measuring optical transfer characteristics through a fluid sample, although many other types of sensor could be used dependent on the application of the analytical device 20.

The electromechanical subassembly 26 can be configured to receive sample ampoules or cassettes and load them into a specimen processing section 28 so that they can be analyzed by the sensor device 24. Following analysis, the electromechanical subassembly 26 may eject the sample ampoules or cassettes.

The specimen processing section 28 may perform pre-analysis functions such as agitation or heating of the sample to a required analysis temperature.

The analysis unit 30 may receive data from the sensor device 24 comprising a characterization of a specimen contained in the specimen processing section 28. The analysis unit 30 may perform one or more data processing operations on the data from the sensor device 24. For example, the analysis unit 30 may ensure that the result from the sensor device 24 is within expected boundaries.

Following analysis, the analysis unit 30 may transmit data from the sensor device 24 via the communications and control unit 32 to the system for analytical device management via the communications network 21, and eventually to a data processing agent 23 hosted on, for example, a server.

A skilled person can appreciate that the foregoing description of a generic analytical device 40 is provided for illustrative purposes, and that practical analytical devices may comprise fewer or more modules and functionalities.

In an example, the analytical device 20 can be configured to perform blood glucose testing, coagulation testing, blood gas and electrolyte analysis, urine analysis, cardiac marker analysis, haemoglobin analysis, infectious disease testing, cholesterol screening or nucleic acid testing. Several functional and/or operational aspects of the analytical devices P1A-P7A can be configurable or customizable using one or more analyzer parameters.

In an example, the analytical device 20 can be configured to receive data from, for example, a camera or microphone and to analyze the data for medically relevant indications.

The one or more analytical devices 20 (P1A-P7A in the network 10A, 19B) can generate a wide range of automatic notifications and transmit them over the communications network 21 to a data processing agent 23. One or more modules of the analytical devices P1A-P7A may be configured to generate different types of automatic notification (for example, event data, results data, calibration data, and maintenance-related data).

For example, the power supply 22 may generate the automatic notification "batt_lo_10%" to indicate that the power supply 22 only has 10% of its capacity remaining.

For example, the power supply 22 may generate the automatic notification "batt_shutdown" to indicate that the power supply 22 only has shut down the battery owing to a battery fault, or having run out of battery power.

For example, the electromechanical subassembly 26 may generate the automatic notification "motor_PCB_HB" as a repetitive "heartbeat signal" indicating that it is continuously functional.

For example, the sensor device 24 may generate a photometer printed circuit board "heartbeat" signal. In addition, the sensor device 24 may generate the automatic notification "photometer_clean_warn" indicating that the on-board LED and/or laser requires cleaning.

For example, the specimen processing section 28 may report the automatic notification "door_jam" to signal that a sample-handling door of the analytical device has not closed to contain the sample securely.

For example, the control and communications unit 32 may generate an automatic notification in the form of a "temp_hi_90%" signal indicating that the operating temperature of the analytical device is approaching an unsafe temperature at which inaccurate results may be provided. For example, the control and communications unit 32 may generate automatic notifications in the form of a "temp auto shutdown" signal indicating that the analytical device 20 has been switched off owing to an excessive temperature.

The control and communication unit 32 may also transmit automatic notifications as sequence of analysis states ("scan_barcode", "report_barcode", "assay_loaded", "test_result") to enable the status of individual tests to be tracked.

The control and communication unit 32 may provide automatic notifications reporting on software configuration aspects of the analytical device 20 such as the state of internal memory, a current software or firmware version, and security parameters such as the success or failure of passwords, and networking aspects such as reporting network configuration settings, the network or MAC address of the analytical device, and optionally network uptime and downtime.

Optionally, the automatic notification can be time stamped by the control and communication unit 32 to an accuracy of about 10 seconds, about one second, about 0.1 s, about 0.01 s, or an even higher accuracy as enabled by, for example, the Ethernet time protocol or network time protocol. This can enable a data processing agent 23 hosted by a remote server to reconstruct the sequence of received automatic notifications relative to the time that an event occurred triggering the generation of the automatic notifications.

Of course, the control and communication unit 32 may generate more complicated automatic notifications comprising concatenated groups of individual automatic notifications, based on rules contained in the control and communications unit 32 of the analytical device 20.

Optionally, the automatic notification may be concatenated with test result data obtained from the analysis of a patient sample.

The automatic notification can be transmitted as a data packet encapsulated according to a protocol of the communication system 16A used in the system for analytical device management, as known by persons skilled in the art. The data packet can comprise the automatic notification, and may comprise any necessary arrangement of header information to enable reliable routing of the automatic notification to the data processing agent.

The data packet may comprise only one bit of payload information (for example in the case of a heartbeat flag).

Alternatively, the data packet may comprise a large amount of information (for example, several kilobytes or megabytes, in the case of an image or an accelerometer or audio recording made over a long period of time). The control and communications unit 32 of the analytical device 20 may be configured to buffer a plurality of automatic notification messages for a given amount of time, and to concatenate the messages into one data packet, for example. This may lead to longer battery life of a handheld analytical device.

In an example, the automatic notification can be a communication compliant with the "HL7" protocol (Health Level Seven, Ann Arbor MI, USA) and/or the ASTM protocol (for example, ASTM 1394 LIS2).

A skilled person can appreciate that the foregoing description of an analytical device 20 can also apply to the analytical devices P1B-P7B communicatively coupled to the further communications network 10B. The techniques of the present disclosure can be applied to a range of different types of analytical device, which may have a different distribution of sensors, actuators, and components to those described above. Identification of the type of an analytical device by a central system can be achieved using a manufacturer identification code, network address, MAC address, and the like.

Figure 4:
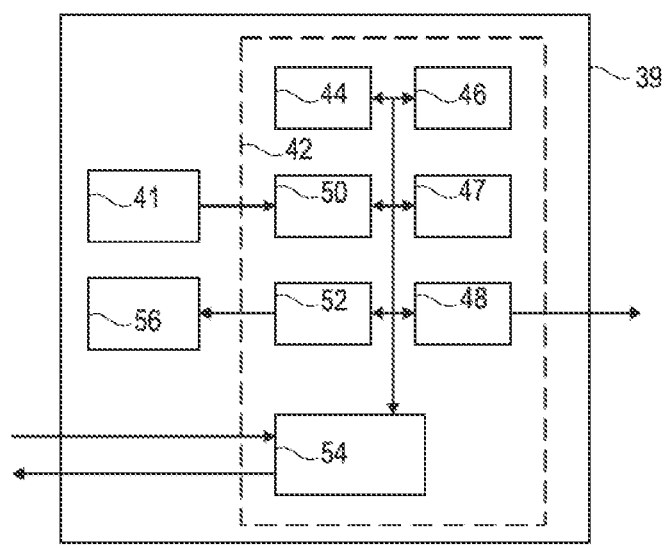
FIG. 4 illustrates schematically an example of an apparatus (server) configured to host a data processing agent according to an embodiment of the present disclosure.

FIG. 4 schematically illustrates an example of a server 40 configured to host a data processing agent.

In this example, the server 40 can comprise a motherboard 42 comprising a random access memory (RAM) 44, a read-only memory (ROM) 46, a central processing unit (CPU) 47, an input/output interface 48, a data storage interface 50 (such as, for example, an interface to a non-volatile memory 49), a display interface 52, and a communication interface 54, however a skilled person can appreciate that many different types of server configuration can be provided with more or fewer modules having other functionality.

The central processing unit (CPU) 47 of the server 40 can be configured to obtain, from an interfaced non-volatile memory 49 (for example), computer readable instructions which, when executed, can instantiate a data processing agent for inferring a condition of at least one analytical device P1A-P7A, P1B-P7B in a network 10 in the random access memory (RAM) 44 of the server 40.

The communication interface 54 of the server can be configured to interface with the communications network 21. Automatic notifications from an analytical device P1A-P7A can be received at the server 40 via the communication interface 54 of the server.

Optionally, the automatic notification can be provided directly to the random access memory (RAM) 44 by processing and analysis by the central processing unit 47. Optionally, the automatic notification can be written to the non-volatile memory 49 for subsequent analysis.

Optionally, the automatic notification may be written (i.e., cached) to an external file store (not shown). On demand by the central processing unit (CPU) 47, a request for the automatic notification may be sent to an external file store over the communications network 21. The external file store may, pending authentication and authorization, transmit at least one automatic notification to the server 40, where it may be subsequently processed.

The benefit of the foregoing optional embodiment can be that a large amount of automatic notifications may be robustly stored until they need to be processed. It may not be essential that the condition of an analytical device is inferred at the same time that the analytical device notification is received.

Alternatively, the inference may be performed in a post-processing step using, for example, timestamp data of the automatic notification.

Optionally, an inferred condition of an analytical device can be updated or generated immediately when an automatic notification is received by the data processing agent.

The data processing agent 23 can be instantiated on the server 40 from machine-readable instructions obtained, for example, from the random access memory (RAM) 44, or the read-only memory (ROM) 46, the input/output interface 48, or the data storage interface 50.

The data processing agent 23 can therefore be configured to receive one or more automatic notifications. The data processing agent 23 instantiated on the server 40 can be configured to generate an automatic notification reporting the inferred condition of one or more analytical devices P1A-P7A, P1B-P7B, in one or more networks 10A, 10B, based on techniques to be discussed subsequently, and to transmit at least a notification reporting the inferred condition as a data structure (signal) to one or more further point of care devices P1B-P7B communicatively coupled to a further communications network 10B, and/or to a POC-DMS 12A, 12B.

Optionally, the server 40 hosting the data processing agent 23 can be configured to display an inferred condition of an analytical device HA-P7A to a user on a local display via a local display driver 56, or by communicating the inferred condition to a further device such as a smart phone 26A.

A computer-implemented method 60 for inferring a condition of at least one analytical device P1A-P7A, P1B-P7B based on at least one automatic notification received over a network 21 from the analytical device can be provided. The method can comprise receiving 61, at a data processing agent 40, at least one automatic notification from at least one analytical device, processing 62, at the data processing agent 40, the at least one automatic notification, to thus identify one or more characteristics of the automated analyzer based on the at least one automatic notification, from the at least one analytical device; inferring 63, at the data processing agent 40, the condition of the at least one analytical device, by applying the one or more identified characteristics to a model; and generating 64, at the data processing agent 40, a notification reporting the inferred condition of the analytical device.

Figure 5:
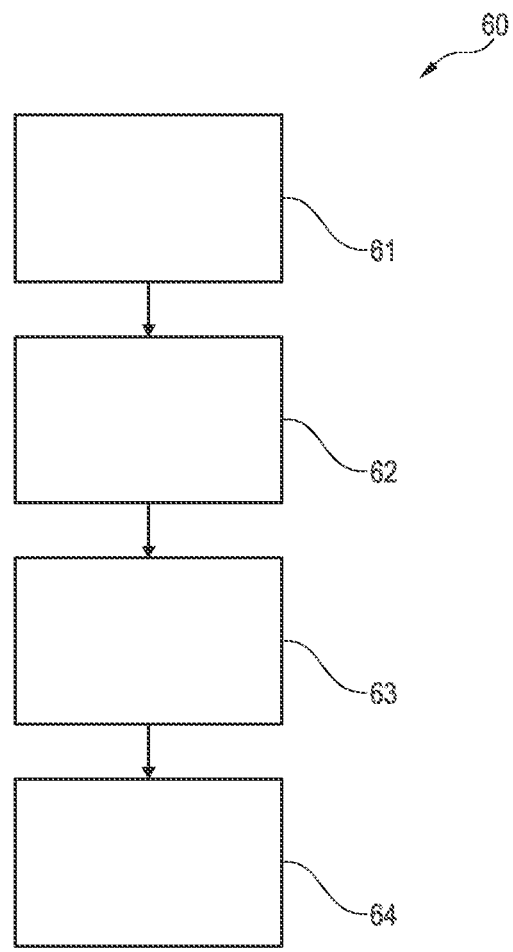
FIG. 5 illustrates schematically a method according to an embodiment of the present disclosure.

FIG. 5 schematically illustrates the computer-implemented method.

Figure 6:
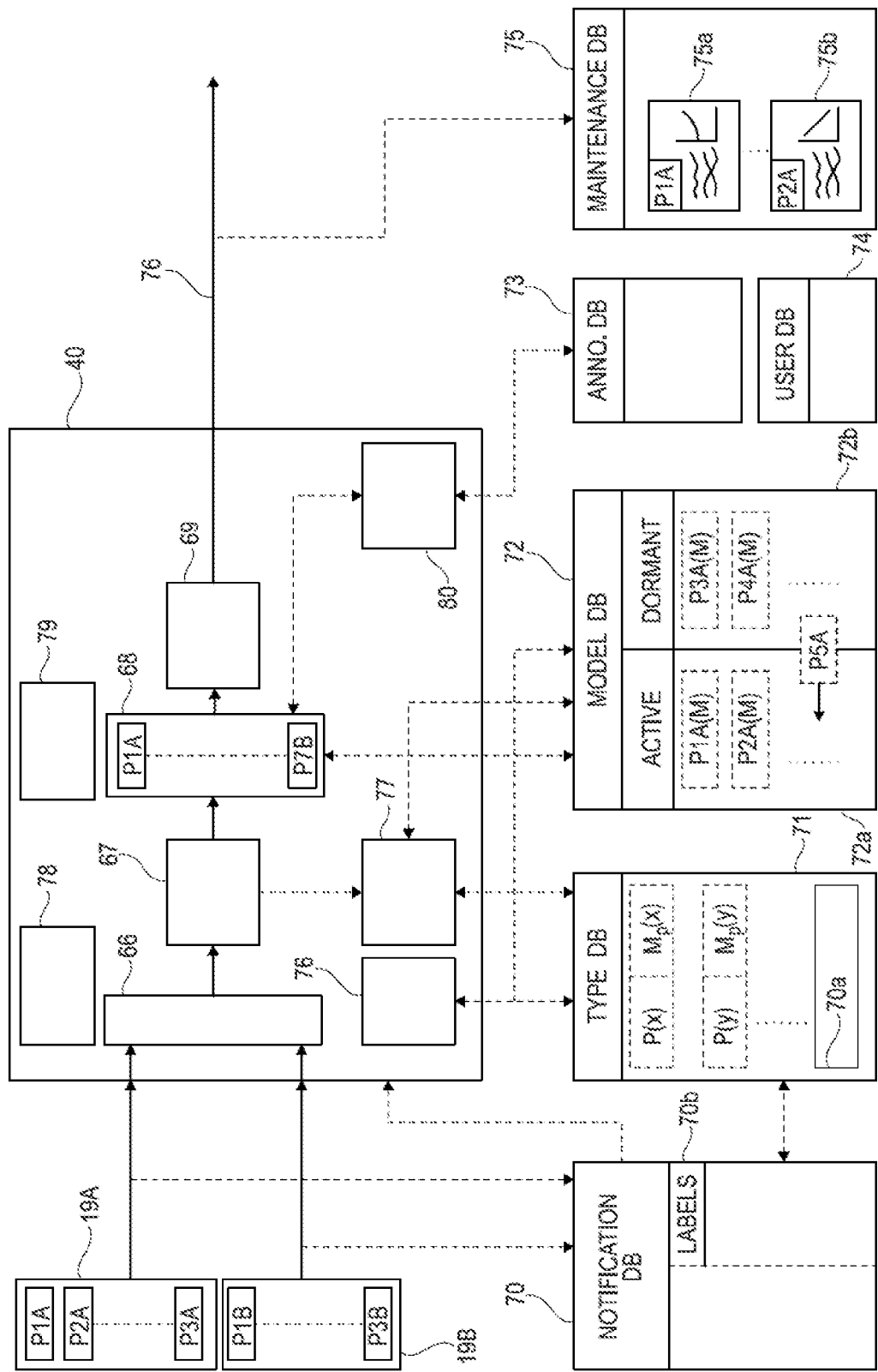
FIG. 6 illustrates schematically a logical environment of the data processing agent when executed on a processor or other processor types according to an embodiment of the present disclosure.

When executed on a server processor or other processor means, the data processing agent configured to carry out the claimed method may interface with one, or more databases, as illustrated in FIG. 6.

FIG. 6 schematically illustrates one example of a logical environment of the data processing agent 40 when executed on a server processor or other processor means. The logical environment representation of FIG. 6 aims, for convenience, to exemplify the internal and external context of the data processing agent in its operational context. However, the absence of a connecting line between elements or the position of an element in FIG. 6 is not to be construed as limiting.

The analytical devices P1A-P7A, P1B-P7B in hospitals 19A, 19B can be communicatively coupled to data processing agent 40 (executing, for example, on a server or a cloud service).

The data processing agent 40 can comprise a receiving engine 66 configured to interface with a network 10 and to receive automatic notifications from the network. Alternatively or in addition, the receiving engine may interface with a notification database 70 to access past notifications. The receiving engine 66 can optionally perform pre-processing to prepare the automatic notifications for processing by removing unnecessary fields in the automatic notifications, for example.

Optionally, the receiving engine 66 can be configured to subsample the automatic notifications from the network 10. For example, the receiving engine 66 may subsample automatic notifications so that notifications from analytical devices of the same type are received. According to this option, the maintenance condition of a specific type of analyses may be tracked or inferred, for example all analytical devices from a given manufacturer.

Optionally, the receiving engine 66 may subsample automatic notifications so that notifications referring to a subclass of messages of the same type can be received. For example, a maintenance provider primarily interested in battery replacement and reliability may opt to base the processing of the data processing agent on messages relating to battery health, as one example.

Optionally, the receiving engine 66 may subsample automatic notifications so that notifications from one targeted analytical device in the network 10 can be received. According to this option, the maintenance condition of one specific targeted analytical device may be tracked or inferred.

The data processing agent 40 can comprise an identification engine 67 configured to receive pre-processed automatic notifications from the receiving engine 66 and/or the notification database 70. The identification engine 67 can be configured to analyze one, or more of the automatic notifications to identify a characteristic of the automatic notifications.

In an example, a characteristic in the plurality of automatic notifications can be some combination, or arrangement of the automatic notifications, that can enable an inference about the condition of the analytical device to be performed. In an example, the characteristic can be a subset of the set of automatic notifications received by the data processing agent 40 that can be related to an effect or condition of the analytical device.

In practice, the one or more identified characteristics may comprise a subset of the automatic notifications transmitted by the at least one analytical device in the network 10.

Optionally, the relative time relationship between the notifications in the subset of automatic notifications can be recorded or preserved, to enable an inference about the condition of an analytical device to be made. Optionally, the identified characteristic may comprise a histogram of different types of automatic notification received over a given time window, for example.

For example, a set of repeated automatic notifications of the same type advising of multiple "door jams" affecting analytical device P1A can be one example of a characteristic pattern, however a characteristic pattern of the automatic notifications may be composed using other more complicated rules combining automatic notifications of more than one type, or windowing automatic notifications according to a specific time window. The one or more identified characteristics may, an example, be viewed as a filtered, reduced, or summarized version of the automatic notifications received from the network 10 that can be used as the input to an inference process.

The data processing agent 40 can comprise an inference engine 68. The inference engine 68 can be configured to receive one or more identified characteristics from the identification engine 67. By applying the one or more identified characteristics to a model, information about the condition of at least one analytical device P1A can be inferred.

The data processing agent 40 can comprise a notification generator 69. If the inference engine 68 applies the identified one or more characteristics to its model and subsequently infers that the analytical device P1A is in a condition that requires a notification to be generated, the notification generator 69 can generate a notification relating to the condition of analytical device P1A.

The notification may be a data record defining a relatively simple inference, such as "80% chance of battery failure in POC P1A in the next week". Alternatively, the notification may be a data structure defining a range of conditions of the one or more analytical devices P1A-P7A at a past, present, or future time (as predicted by the model) of the analytical device P1A that may be useful to a maintenance technician, for example.

The data record or data structure generated by the notification generator 69 may be stored in a database, such as maintenance database 75. The data record or data structure generated by the notification generator may be communicated to one or more POC-DMS computers 12 in the network 10 to enable an operator to obtain an overview of the maintenance condition of one or more analytical devices in the network 10.

Optionally, the inference engine 68 can execute a corresponding number of models to the number of analytical devices P1A-P7A in the network 10A. Optionally, the inference engine 68 can execute a plurality of different types of model, wherein the types of model executed by the inference engine 68 can correspond to the types of analytical devices P1A-P7A operating in the network 10A.

Optionally, each model executed by the inference engine 68 can track an aspect of the condition of corresponding analytical device P1A operating in the network 10A.

Optionally, when a first analytical device P1A is connected to the network 10A, a corresponding first model can be instantiated in the inference engine 68. As the data processing agent 40 receives automatic notifications from the first analytical device P1A, the inference engine 68 can iterate at least an aspect of the inferred condition of the first analytical device P1A, defined by the model 68, based on the received automatic notifications. When the first analytical device P1A is removed from the network 10A, the first model can be stored and removed from the inference engine 68. Accordingly, in an embodiment the model 68 can be a composite model with a composition that can be reflected by the analytical devices that are currently connected to the network 10.

Optionally, the notification generator 69 can be configured to transmit the notification reporting the inferred condition to a POC management computer 12A, 12B.

Optionally, the notification generator 69 can be configured to transmit the notification reporting the inferred condition to a maintenance database 75.

The data processing agent 40 can comprise a number of ancillary logical engines that may not be essential, but may nevertheless can provide advantageous properties to embodiments.

The data processing agent 40 may comprise a network-monitoring engine 78. The network-monitoring engine 78 can be configured to probe the network 10 to identify analytical devices P1A-P7A, P1B-P7B connected to the network 10. Alternatively or in addition, the network-monitoring engine 78 may interrogate a device registry maintained by, for example, a POC-DMS 12A. Therefore, a register of active devices and historically active but presently dormant devices can be constructed. Optionally, the network monitoring engine 78 can use a protocol such as Simple Network Management Protocol version 3 (SNMP v.3) to investigate the hierarchy of the network 10 and to identify relevant analytical devices. The network-monitoring engine 78 can enable the data processing agent 40 to maintain an accurate impression of the analytical devices presently connected to the network 10.

The data processing agent 40 may comprise an annotation engine 80. The annotation engine 80 can be configured to obtain annotation data. Annotation data can be, for example, unstructured or semi-structured text entered by a health professional such as a point-of-care device manager into the POC-DMS. Annotation data may refer to free text comments such as "Mar. 20, 2019—POC P3A needs its sensor cleaning—please clean overnight". The annotation data may be fused with the automatic notification data received from the analytical devices, or used to identify one or more characteristics of at least one automatic notification, or to infer a condition of at least one analytical device. Accordingly, the annotation engine 80 can be configured to interrogate an annotation database 73 to obtain and process relevant annotations, before using the annotations in combination with processes in the identification engine 67 or the inference engine 68. This may allow automatic notifications to be better technically contextualized, for example.

The data processing agent 40 may comprise a model generator 79. Based on received automatic notifications, the model generator 79 may be configured to adjust or recalculate a model used to generate an inference of the condition of an analytical device. The model generator 79 may apply a machine-learning approach to input automatic notifications. The model may be obtained using one or more of a rules-based model, a linear regression, a decision tree, a support vector machine, a k-nearest neighbor model, a random forest model, an auto encoder, a convolutional neural network, a recursive neural network, a deep belief network, or a transfer-learning model. It may not be essential that a model is generated using machine learning. A fixed model, based on predefined logical rules, may be provided in the inference engine 68.

The model may characterize the behavior of one or more functions of an analytical device in the network 10. The model may comprise sub-models: in other words, a model of a first type can be used to track the power supply performance of an analytical device, and a model of the second type can be used to track the mechanical and/or sensor subsystem of an analytical device.

The data processing agent 40 may comprise an analyzer type monitor 76. The purpose of the analyzer type monitor 76 can be to identify, for each analytical device P1A-P7A, P1B-P7B connected to the network 10, the unique manufacturer model of the each analytical device P1A-P7A, P1B-P7B. Accordingly, the network-monitoring engine 78 may detect the connection of an unknown analytical device P3B to the network 10. The network-monitoring engine 78 may signal to the analyzer type monitor 76 that an unknown analytical device P3B has been connected to the network 10. The analyzer type monitor 76 may obtain identifying information from the unknown analytical device P3B. The analyzer type monitor 76 may obtain the identifying information either by direct interrogation of the unknown analytical device P3B, or by passive monitoring ("sniffing") of automatic notifications from the unknown analytical device P3B. For example, the identifying information may be a manufacturer identification code, or a firmware version code.

The analyzer type monitor 76 may then interface with an analyzer type database 71 to assign an analytical device type to the unknown analytical device P3B.

The data processing agent 40 may comprise an analyzer characteristic detection engine 77. The function of the analyzer characteristic detection engine 77 can be to identify, in a large plurality of automatic notifications, patterns of automatic notifications that are unique, or have a high likelihood of identifying, a fixed type of analytical device. Accordingly, for each type record P(x) in the analyzer type database, there can be an associated analyzer automatic notification alphabet Mp(x). The analyzer automatic notification alphabet Mp(x) can characterize the set of automatic notifications that a given analyzer may transmit.

Furthermore, each type record P(x) in the analyzer type database may also comprise a set of characteristics (such as a combination of automatic notifications of various types, at various time spacings) that potentially characterize a technical condition or event of an associated analytical device. One effect can be that monitoring for a set of characteristics can enable conditions or events to be identified from a larger set of automatic notifications received at the data processing agent.

Furthermore, the data processing agent 40 may interface with one or more ancillary databases that are not essential, but may nevertheless provide advantageous properties to embodiments. The ancillary databases are now described.

A notification database 70 can comprise a plurality of analytical device notifications received from analytical devices P1A-P7A, P1B-P7B connected to the network 10. In one embodiment, the data processing agent 40 can process live data from the network 10. In another embodiment, the data processing agent 40 may process historical data stored in the notification database 70.

Optionally, at least one automatic notification in the notification database 70 can be associated with a label 70b. For example, a user may view a set of automatic notifications in the notification database 70b associated with an identified maintenance fault in an analytical device P1A. The user may define a label that the set of automatic notifications identified are associated with the identified maintenance fault.

A plurality of automatic notifications sent by analytical devices P1A-P7A, P1B-P7B can be optionally stored in notification database 70. The notification database 70 can store all historical automatic notifications from all automatic analyzers P1A-P7A, P1B-P7B. The notification database 70 can alternatively store automatic notifications from a subset of the analytical devices P1A-P7A.

Optionally, the notification database 70 can delete automatic notifications according to a deletion criteria (such as if a notification is over a certain age, for example).

Optionally, for at least one type of automatic notification, one or more characteristic patterns 70a of the automatic notifications may be defined either prior to operation of the data processing agent, or during operation of the data processing agent, and stored, for example, as a related table in the notification database 70. The one or more characteristic patterns can enable the identification of one or more characteristics using the automatic notifications transmitted from one or more analytical devices.

An analyzer type database 71 can store a set of data records defining a set of types of analytical device that may be used on the network 10. For each analytical device type record P(x) in the analyzer type database, there can be an associated analyzer message alphabet Mp(x). For each analytical device type record P(x) in the analyzer type database, there may be provided an initial model or plurality of initial sub-models defined by a manufacturer of an analytical device.

Optionally, one or more characteristic patterns 70a from the type database 70 may be compared to incoming automatic notification data to identify one or more characteristics of the at least one notification.

For example, if the identification engine 67 communicates an identified characteristic of the automatic notifications that one automatic notification reporting a "door jam" is issued by analytical device P1A every three months, on average, the model may enable an inference that the condition of the analytical device P1A can be such that the door mechanism does not require maintenance. However, if the identification engine 67 communicates an identified characteristic of the automatic notifications that over one in three assays results in an automatic notification reporting a "door jam" from analytical device P1A, the model applied by the inference engine 68 may classify P1A as being at a higher risk of a door mechanism failure, for example.

The initial model can define, for example, the expected condition of a type of analytical device to which the initial model can refer when in an unused condition, or after a given number of hours of use.

The model database 72 can function for example, as a registry of models of analytical devices that are, or have been, active in the network 10. The model database 72 can be, in an example, divided into an active analyzer partition 72a and a dormant analyzer partition 72b. In the illustrated example, analytical device P5A has recently been connected to the network 10 as identified by the network-monitoring engine 78, and thus its model record can be moved from the dormant partition 72b to the active partition 72a.

When an analytical device P1A is connected to the network 10, and its accompanying model P1A(M) in the model database 72 can be in the active partition 72a, the model P1A(M) can be updated so as to track a current condition of one or more aspects of the analytical device P1A inferred by the inference engine 68 based on characteristics in the automatic notifications identified by the identification engine 67. In other words, the model P1A(M), when in the active partition of the model database 72a, can reflect the technical condition of the analytical device P1A in one or more respects. For example, the technical condition of a photometer sensor may be inferred from the number and combination of "photometer clean" messages received over time.

In an example, the model P1A(M) may track at least the battery condition of the analytical device P1A. When the network monitoring engine 78 detects the connection of analytical device P1A to the network 10, the accompanying model P1A(M) holding the previous battery charge characteristic can be moved from the dormant partition 72b of the model database 72 to the active partition 72a.

The model P1A(M) may contain information not only on the present charge of the battery of the analytical device P1A, but also historical information concerning the charging time and intensity. For example, repeated use of short charging durations can prematurely reduce the conductivity of certain types of battery. In this example, the inference engine 68 may infer a charging condition based on characteristics identified by the identification engine 67. The inference engine 68 may update a model P1A(M) to track battery charging durations. Subsequently, this can enable the notification generator to generate a warning if the battery of the analyzer P1A was at risk of degrading faster than expected owing to the charging behavior.

An annotation database 73 can store records comprising unstructured or semi-structured annotations provided by laboratory or other medical personnel. Fusion of the records in the annotation database with the automatic notification data received from the analytical devices may improve the accuracy of the notifications reporting the inferred condition of the analytical device.

Optionally, the identification of one or more identified characteristics in the plurality of automated notifications can be performed based on a comparison between a portion of the annotation data, and the plurality of automated notifications. For example, a subset of automated notifications may be selected for a subsequent inference step using a model based on portion of the annotation data. For example, an annotation comment referring to a battery fault at a specific time may be used to window the plurality of automated notifications to the automated notifications received at, or proximal, to the specific time. The type of automated annotations may be subsampled based on the annotation data. For example, an annotation concerning battery health may cause the identification of one or more identified characteristics to be based on a subset of automated notifications connected to the battery.

Optionally, the inference of a condition of at least one analytical device may be influenced based on the annotation data. For example, the annotation data may be provided to the input layer of a machine-learning model. The automatic notifications may be provided to the input layer of the same machine-learning model. The model may be trained based on both the annotation data and the automatic notifications.

A user database 74 can comprise a register of permitted users of one or more analytical devices in the network 10. In an example, automatic notifications received from an analytical device P1A may be associated with a user record in the user database 74. Accordingly, analytical device maintenance trends based on one or more users of the analytical devices P1A-P7A, P1B-P7B may be detected. Appropriate anonymization of the user database 74 may be provided to ensure confidentiality.

A maintenance database 75 can comprise a maintenance record 75a, 75b for at least one analytical device elected to the network 10, or that has historically been connected to the network 10. Optionally, a group of analyzers at the same hospital site 19A may be maintained in a joint maintenance record. The maintenance record 75a can define, for analytical device P1A, the expected maintenance state of aspects of the analytical device P1A based on the model P1A(M), as updated in use based on the automatic notifications received from the analytical device P1A. The maintenance record 75a may enable the generation of a report containing advisory or compulsory maintenance actions for one or more analytical devices in the network 10 based on the status of the one or more models in the active model database 72a or the dormant model database 72b. For example, the report can provide a visual representation of the expected location on a "bathtub reliability curve" of a plurality of replaceable analytical device components.

The operation of an example of the data processing agent 40 will now be discussed.

A user may connect an analytical device P1A to a network 10A. A data processing agent 40 executing on server 23 can also be communicatively coupled to the network 10A via communication network (e.g., wide area network) 21. The network-monitoring engine 78 can detect the connection of the analytical device P1A to the network 10A. The network-monitoring engine 78 can inform analyzer type monitor 76 of the connection of analytical device P1A to the network 10A. Analyzer type monitor 76 can receive at least one automatic notification from analytical device P1A via the receiving engine 66. Analyzer type monitor 76 can identify an identifier, such as a manufacturer code of the analytical device P1A in the at least one automatic notification, and can look up the assigned type of the analytical device P1A in the type database 71. The analyzer type monitor 76 can further look up the identifier in the model database 72.

In the case that the identifier refers to a type of analytical device P1A that is not present in the dormant division 72b of the model database 72, the data processing agent 40 can obtain a copy of the model P1A(M) of the type of analytical device P1A referenced by the identifier, and can instantiate the copy of the model P1A(M) in the active division of the model database 72. Furthermore, the copy of the model P1A(M) can be linked to the inference engine 68 of the data processing engine 40 so the changes made to the model P1A(M) by the inference engine 68 reflecting one or more aspects of a current condition of the analytical device P1A can also be dated in the active section 72b of the model database 72.

An alternative case can be that the identifier can refer to an analytical device P3A with a model that can be present in the dormant division 72b of the model database 72. This can mean that the analytical device P3A can have already been used in the network 10. In this case, the model P3A(M) can be moved into the active division 72a of the model database 72 and can be instantiated in the inference engine 68.

The receiving engine 66 can continuously receive automatic notifications from the analytical device P1A. In this example, the identification engine 67 can continuously monitor the received automatic notifications to identify at least one characteristic in the received automatic notifications. For example, the identification engine 67 may identify a sequence of six "battery low" warnings within a given time period and assert a logic flag in the data processing agent 40 if the characteristic is identified in the plurality of automatic notifications from analytical device P1A.

The model P1A(M) in the inference engine 68 may comprise a sub-model configured to infer the condition of the battery status of analytical device P1A. Upon assertion of the logic flag representing the sequence of six "battery low" warnings within a given time period, the P1A(M) in the inference engine 68 can be updated to model the effect of the occurrence of the six "battery low" warnings within a given time period on the analytical device P1A. For example, a "time to battery replacement" variable related to the door mechanism may be decremented, and/or a condition variable reflecting the condition of the battery of analytical device P1A may be updated to reflect an increased chance of accelerated battery failure.

The notification generator 69 can be, in this example, configured to generate a notification reporting the increased chance of accelerated battery failure. The notification generator 69 can generate a new maintenance record for the newly connected analytical device P1A and can enter the notification reporting the increased chance of accelerated battery failure into the report.

Eventually, a user may power-down or disconnect the analytical device P1A from the network 10A. This action can be detected by the network-monitoring engine 78 and reported to the data processing engine 40. In response, the current state of the model P1A(M) in the inference engine 68 (and the accompanying entry of model P1A(M) in the active partition 72a of the model database 72 can be frozen. The model P1A(M) (containing at least an accurate summary of the battery condition of analytical device P1A) can be copied to the dormant partition 72a of model database 72, until the analytical device P1A is reconnected to network 10A.

Figure 7A:
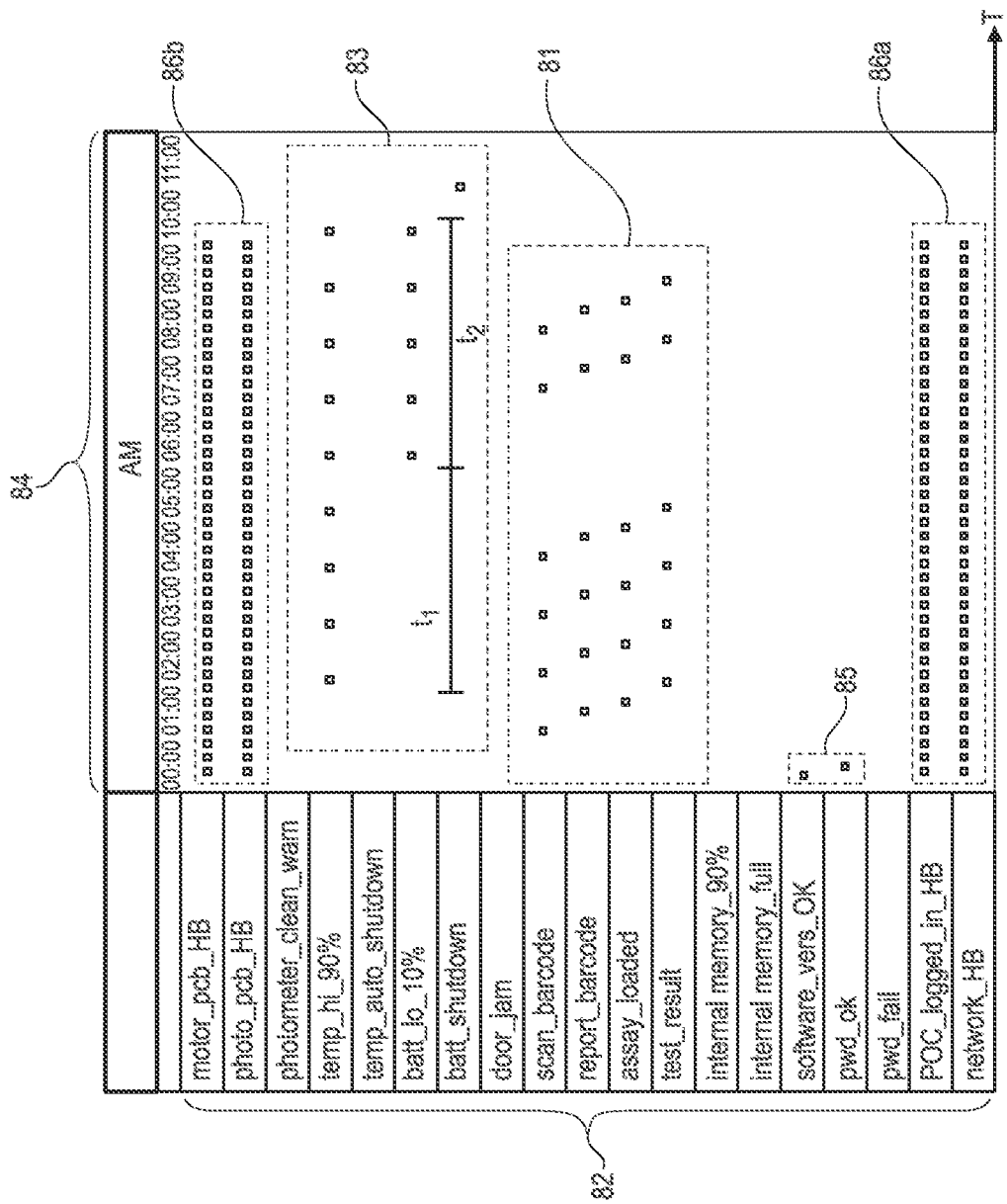
FIG. 7a illustrates schematically an example of identification of a characteristic and the subsequent inference of a condition of an analytical device according to an embodiment of the present disclosure.

FIG. 7a schematically illustrates an example time-event plot of the identification of a characteristic and the subsequent inference of a condition of an analytical device. The time axis 84 can show the duration of a typical shift in a POC context. An example of a set 82 of different types of automatic notifications can be plotted against the time axis 84 to illustrate an example of an automatic notification flow from an analytical device. Each square entry in the time-event plot represents the transmission of one data packet over a network 10 from an analytical device P1A.

In one example, all of the received automatic notifications may be provided directly to a model Mp(x), and the model may directly infer a condition of an analytical device. For example, the model may be a deep learning model generated using a convolutional neural network as one option. Accordingly, the step of identifying one or more characteristics of the analytical device can be based on the at least one automatic notification, from the at least one analytical device according to the first aspect can be, in some embodiments, not essential. The inference of the condition of the at least one analytical device P1A may be made based on all received automatic notifications, or on a subsample of all received automatic notifications.

A first group (subset) of automatic notifications 81 can represent an example of characteristic of six assays being performed, with the automatic notifications "scan_barcode", "report_barcode", "assay_loaded", and "test_result" issued in sequence for each assay performed.

A second group of automatic notifications 83 can represent an example of a characteristic of a development of a battery fault. Many types of battery carry a small risk of battery unreliability, and detection of a developing battery fault may be desirable. For example, the occurrence of repeated "temp_hi_90%" signals alone may only imply that an analytical device P1A has been left on a sunny windowsill. However, a battery failure condition may be denoted by the occurrence of repeated "temp_hi_90%" and, after a predetermined time period $t_1$, the occurrence of repeated "batt_low_10%" notifications, and eventually a single "batt_shutdown" notification, indicating that a battery is overheating because it is discharging too quickly. The speed of onset between the first "temp_hi_90%" and the first "batt_low_10%" notification may enable the severity of the battery failure to be modelled.

Identifying the "temp_hi_90%", "batt_low_10%", and "batt_shutdown" messages may, thus, be the identification of a characteristic of a subset of the automatic notifications that can subsequently be input into a model.

A third group of automatic notifications 85 can represent startup activity of an analytical device.

A fourth group of automatic notifications 86a, 86b can represent "heartbeat" signals denoting normal operation of an analytical device.

A skilled person can appreciate that this specific example of a set of automatic notifications in a specific case is not limiting. Many different characteristics may be identified using different categories of automatic notification from one, or more, analytical devices. For example, automatic notifications from two different analytical devices P1A and P2A indicating a quality control failure may be detected. Such a set of automatic notifications can be a characteristic that may be used to subsequently infer, using a model, that a batch of reagent used in a laboratory is faulty.

In other words, the identification of one or more characteristics of the at least one automatic notification may be viewed as a subsampling of the entire set of received automatic notifications prior to using a model to infer a condition of at least one analytical device.

Figure 7B:
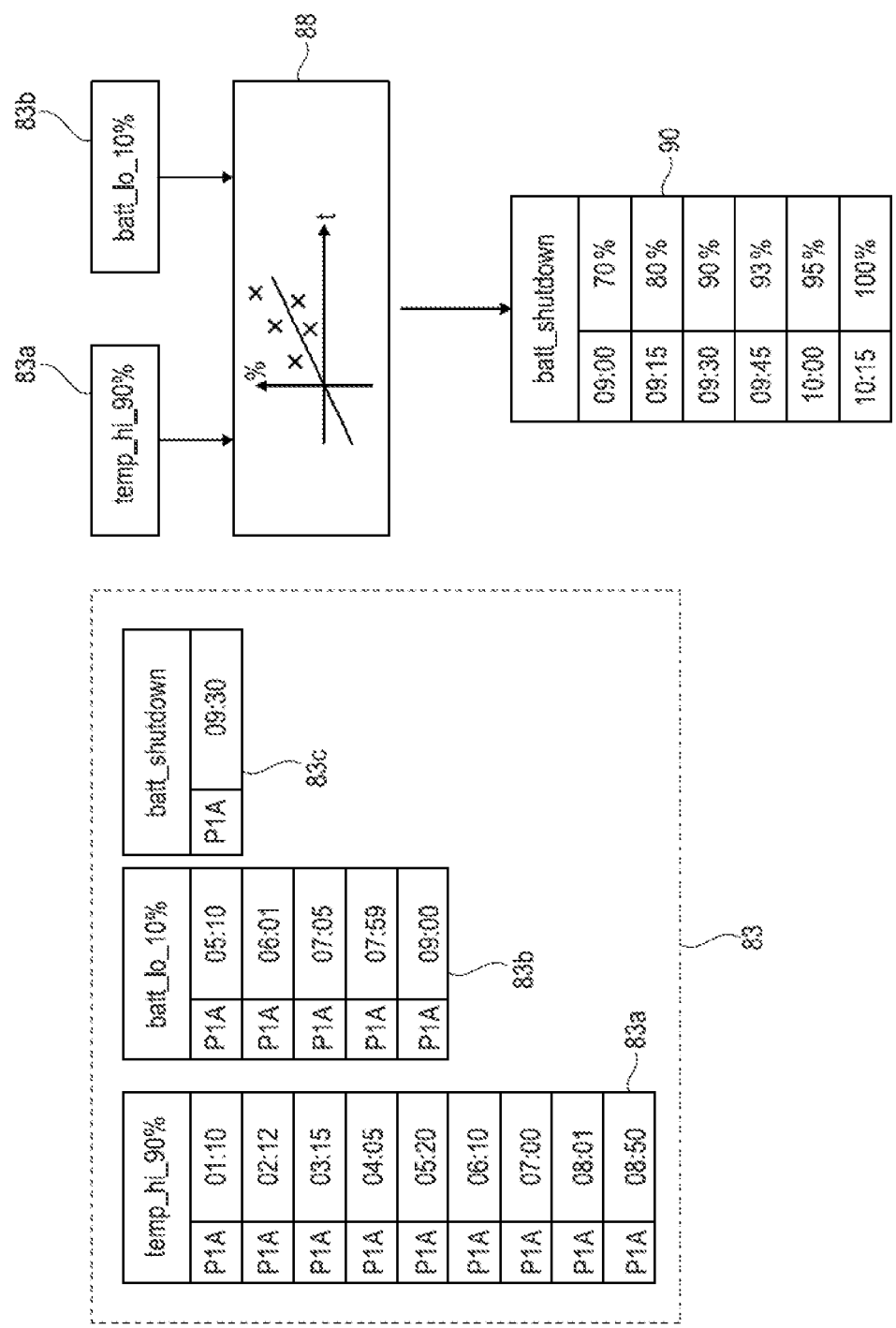
FIG. 7b illustrates schematically the processing of the characteristic of at least one automatic notification identified in the time-event data of FIG. 7a according to an embodiment of the present disclosure.

FIG. 7b schematically illustrates the processing of the characteristic of at least one automatic notification identified in the time-event data of FIG. 7a.

A first data structure 83a can comprise nine automatic notifications from analyzer P1A defining the times at which a "temp_hi_90%" notification was issued. Second data structure 80 3B can comprise five automatic notifications from analyzer P1A defining the times at which a "batt_lo_10%" notification was issued.

During the time from the issuance of the first "temp_hi_90%" notification to the issuance of the "batt_shutdown" notification at 09:30 (implying the shutdown of the analytical device P1A) an inference may be made of the probability of the analytical device shutting down as a result of battery fault. During this time, the one or more characteristics 83a and 83b can be applied to the model 88. The one or more characteristics 83a and 83b can form two time series. By applying the time series to a pre-computed model 88, an inference of the present and/or future condition of the analytical device may be made. In this case, the inference vector 90 can represent a prediction of a probability of time in the shift that the battery will fail, based on the received "temp_hi_90%" and "batt_lo_10%" notifications.

The pre-computed model of battery performance may be obtained from battery manufacturers, or from data captured across the system 10. Optionally, the pre-computed model of battery performance may be generated using an autoregressive integrating moving average modelling technique (ARIMA), a relevance vector machine, a Kalman filter, or a particle filter as one of many choices. The foregoing description can refers to a specific scenario of inferring the likelihood of a battery failure condition, although a skilled person can recognize that the time series data represented by the automatic notifications may be used to infer the conditions of one or more analytical devices in a system 10.

A computer implemented method for generating a model P1A(M) for inferring the state of an analytical device P1A based on a plurality of automatic notifications received from a network 10A can be provided. The method can comprise receiving a plurality of automatic notifications from one or more analytical devices P1A-P7A, P1B-P7B in one or more networks 10A, 10B, at least one subset of the plurality of automatic notifications can be associated with at least one condition of at least one of the one or more analytical devices P1A-P7A, P1B-P7B and training a model Mp(x) using the plurality of automatic notifications as training data to generate the model P1A(M), wherein the model Mp(x) can provide a relationship between the plurality of received automatic notifications and the at least one condition of at least one of the one or more analytical devices P1A-P7A, P1B-P7B.

In an example, the model Mp(x) can be trained or generated using the model generator 79 of the data processing agent 40.

In an example, the model can be trained or generated using time-series data from one or more analytical devices. The model may be trained or generated using an autoregressive integrating moving average modelling technique (ARIMA), a relevance vector machine, a Kalman filter, or a particle filter as one of many choices.

In an example, after training of the model, the model Mp(x) can be stored in the type database 71 and/or the model database 72 the data processing agent 40.

In an example, the model Mp(x) can be associated with a unique type P(x) of analytical device. In an example, the model Mp(x) can be associated with the unique type P(x) of analytical device in a type database 71 accessible to the data processing agent 40.

An example, the model Mp(x) may be trained or generated by an external computer processing means, such as an external server. The model Mp(x) can be transmitted by the external server to the data processing agent 40. After transmission to the data processing agent 40, the model Mp(x) can be stored in the type database 71 and/or the model database 72 of the data processing agent 40.

In an example, the presence of a trigger notification in the plurality of automatic notifications may trigger the data processing agent 40 to train, or retrain, of the model Mp(x) on a subset of automatic notifications representing a characteristic related to the trigger notification.

As an example, in FIG. 7a the notification "batt_shutdown" may serve as a trigger notification to firstly identify historical "batt_lo_10%" and "temp_hi_90" notifications in an arbitrary time window preceding the time that the "batt_shutdown" notification was transmitted. The model Mp(x) may be updated by training or retraining the model based on the identified historical notifications. Advantageously, this can enable models applied to the automatic notifications to adapt to changes in the system 10. For example, in the battery example, if the battery supplier is changed, models relating to the discharge and failure prediction of such batteries can be updated dynamically for one analytical device HA, or for all analytical devices of that type on the network 10.

According to an embodiment of the first aspect, the model can at least partially characterize a type of analytical device P1A-P7A, P1B-P7B used to transmit the at least one automatic notification to the data processing agent 40.

The data processing agent may update a model instance P1A(M) associated with a specific analytical device P1A as the specific analytical device P1A is used, based on received automatic notifications from P1A. Therefore, the model instance P1A(M) may comprise a plurality of sub-models directed to different parts of an analytical device P1A. Sub-models may be provided for one or more of a power supply 22, a sensor device 24, an electromechanical subassembly 26, a specimen processing section 28, and analysis unit 30, enabling tracking of the maintenance condition of the analytical device P1A by reference to the current or historical status of model instance P1A(M).

According to an embodiment, the model can be one, or a combination of, a rules-based model, a linear regression, a decision tree, a support vector machine, a k-nearest neighbor model, a random forest model, an auto encoder, a convolutional neural network, a recursive neural network, a deep belief network, or a transfer-learning model.

According to an embodiment, the method can comprise detecting, at the data processing agent 40, a connection of a further analytical device P1A-P7A, P1B-P7B to the network, and identifying, at the data processing agent 40, if the further analytical device has previously been connected to the network or has not previously been connected to the network.

If the further analytical device has previously been connected to the network, the method can comprise loading, at the data processing agent 40, a stored model for use as the model, wherein the stored model can characterize the condition of the further analytical device at an earlier time that it was disconnected from the network, and processing, at the data processing agent 40, at least one automatic notification from the further analytical device to identify one or more characteristics of the at least one automatic notification from the at least one analytical device. Furthermore, the method can comprise inferring, at the data processing agent 40, the condition of the at least one analytical device, by applying the one or more identified characteristics to the stored model.

According to an embodiment, the method can comprise detecting, at the data processing agent 40, a connection of a further analytical device (P1A-P7A, P1B-P7B) to the network.

If the further analytical device P1A-P7A, P1B-P7B has previously not been connected to the network, the method can comprise identifying, at the data processing agent 40, a type of the further analytical device, instantiating, at the data processing agent 40, an additional model for use as the model, wherein the additional model can be associated with the identified type of the further analytical device; and inferring, at the data processing agent 40, the condition of the further analytical device, by applying the one or more identified characteristics to the additional model.

According to an embodiment, the model can be configured to identify at least one of the following conditions of the at least one analytical device P1A-P7A, P1B-P7B, or their onset: (i) a sensor failure condition, (ii) a condition of sensor unreliability, (iii) a thermal fault condition, (iv) a software or firmware fault condition, (v) a quality control fault condition, (vi) a mechanical fault condition, (vii) a battery fault condition, (viii) a physical shock condition, and/or (ix) a security fault condition.

According to an embodiment, the method can further comprise processing, at the data processing agent 40, the data comprising the at least one automatic notification to identify one or more characteristics of the at least one automatic notification from the at least one analytical device P1A-P7A, P1B-P7B by receiving, at the data processing agent 40, a second automatic notification from the at least one analytical device P1A-P7A, P1B-P7B.

The at least one and the second automatic notifications can be generated by the at least one analytical device P1A-P7A, P1B-P7B at first and second time points, respectively.

The method can further comprise detecting a time relationship between the at least one and the second automatic notifications based on the first and second time points and identifying the one or more characteristics based at least on the detected time relationship.

Optionally, the identification can also be based on the type of the at least one and/or second automatic notification and/or the type of the analytical device from which the at least one and the second automatic notifications originated.

According to an embodiment, the method can further comprise identifying, at the data processing agent 40, one, or more contexts of the at least one analytical device P1A-P7A, P1B-P7B in the network and providing, or updating, the model based, additionally, on the identified context.

Analytical device P1A may be moved, in use, between different wards, laboratories, hospital sites, or even taken on home nursing visits. These can represent different contexts or locations where the analytical device P1A may be used by different personnel, used to generate a different pattern of tests, or used with different sources of reagent, as several examples. The variation in context or locations may lead to different infallible conditions of the analytical device P1A.

For example, the network monitoring engine 78 may identify the source on the network 10 of an automatic notification from analytical device P1A using a variation in network addresses used to access the network 10. For example, a model instance P1A(M) may be supplemented with one or more sub-models representing the use of the analytical device in the one or more different contexts.

According to an embodiment, the method can further comprise receiving, at the data processing agent 40, at least one item of annotation data via the network, associating, at the data processing agent 40, the one or more items of annotation data with one or more of the at least one automatic notifications, and inferring the condition of the at least one analytical device P1A-P7A, P1B-P7B based, additionally, on the association between the at least one item of annotation data with the at least one automatic notifications.

POC administration staff can maintain notebooks logging the condition of one or more analytical devices in their care during a shift. The notebooks can represent an unstructured, or semi-structured source of meta data that may be fused with one or more of the automatic notifications received from one or more analytical devices that may be used to enhance the accuracy of an inferred condition according to the techniques discussed in this specification. For example, each entry in an electronic laboratory notebook can be time-stamped, and thus may be easily correlated in time with the automatic notifications.

In example, keywords of entries in the electronic laboratory notebook may be identified and used to modify the identification of characteristics of the automatic notifications, or to modify the influence of the condition of the analytical device.

Of course, the annotation data may be provided as a non-electronic annotation in a physical lab notebook and converted to annotation data using optical character recognition. The annotation data may be provided as a speech signal is converted to annotation data using speech recognition software.

Figure 8:
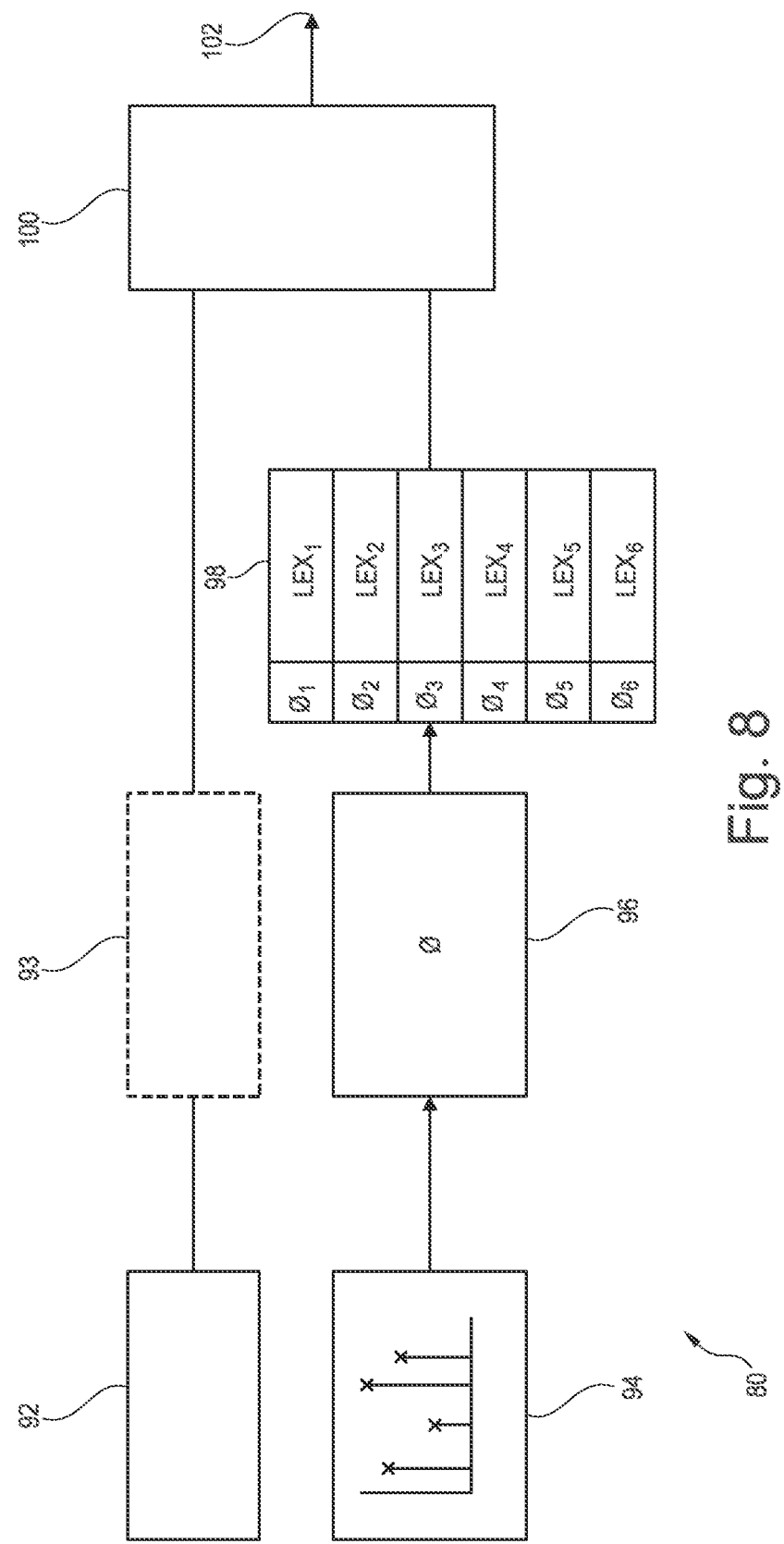
FIG. 8 illustrates schematically an example of an annotation engine for associating automatic notifications with annotation data according to an embodiment of the present disclosure.

FIG. 8 schematically illustrates an example of an annotation engine 80 for associating automatic notifications with annotation data.

The annotation engine 80 illustrated in FIG. 8 is, in an embodiment, implemented as a software engine executing within the data processing agent of the server 12. In another embodiment, the annotation engine 90 may be implemented as a software engine in a remote cloud server, and provide correlated annotation data and automatic notifications to the data processing agent. Annotation data may also be obtained from annotation database 73.

Optionally, the annotation engine 80 may correlate annotation data and automatic notifications in real time (in other words, at the time that the respective data is received at the annotation engine 90).

Optionally, the annotation data and automatic notifications from the analytical device can be correlated or associated based on a time stamp of when the annotation data and automatic notification were created at the analytical device, and/or received at the data processing agent.

Optionally, the annotation data and automatic notifications can be correlated or associated by the annotation engine 80 based on content analysis of the annotation data at the data processing agent, and a comparison with a plurality of automatic notifications received at the data processing agent.

Alternatively, or in addition, the annotation engine 80 may correlate annotation data and automatic notifications in a batch-run at a point in time after the time when the data was received from the analytical device.

The annotation engine 80 can comprise an annotation data reception unit 92. The annotation data reception unit can receive one or more items of annotation data generated, for example, by a user according to one of the modalities discussed above (e.g., reception of unstructured or semi-structured text from a text application, OCR recognition of hand-written comments, recognition of comments from an electronic stylus, audio or video analysis, and the like).

The annotation engine 80 can optionally comprise an annotation data categorization unit 93. Received automatic notifications can be categorized based on, for example, time of receipt, category of message (concerning software configuration, security, authentication, test performance, hardware status, battery status, and the like). The categorization may, for example, be based on a prior semantic schema provided by manufacturer that links different types of automatic notifications to semantic concepts such as "low battery", "clean photometer."

The annotation engine 80 can comprise an automatic notification analysis engine 94. The function of the analysis engine 94 can be to obtain, from a set or subset of the received automatic notifications, a pattern or indication of trends in the automatic notifications that indicate a prior indication of a semantically meaningful event (event data) connected to the analytical device, for example.

In an example, the analysis engine 94 can obtain a histogram of the received annotation data received over a given time window.

In other words, the automatic notifications 94 can function to perform mathematical analysis, or statistical analysis, or signal processing on the received annotation data to, for example, identify significant trends in the data.

Optionally, the time window can be configurable. The time window may be one year, one month, one week, one day, or may be linked to operational considerations such as a shift pattern. Optionally, the time window may be associated with a certified user of the analytical device.

The annotation engine 80 can comprise a significance engine 96. The significance engine 96 can receive event data from the data analysis engine 94. A skilled person can appreciate that a statistical analysis of the automatic notifications may be skewed because some types of relatively insignificant automatic notifications may be transmitted frequently as a normal measure (such as a PCB heartbeat signal). On the other hand, significant automatic notifications may only be transmitted once, for example, a "shock" signal indicating that the analytical device has been dropped on the floor.

Accordingly, the purpose of the significance engine 96 can be to filter the data from the data analysis engine 94 to prioritize significant automatic notifications, according to a prioritization function, which, as a skilled person can appreciate, can be defined as a lookup table or in other ways.

The annotation engine 80 can comprise a lexical transform engine 98. The lexical transform engine 98 can obtain the prioritized analyzer notifications from the significance engine 96 and perform a mapping of significant analytical device notifications to corresponding lexical concept data.

The lexical concept data can be defined by a manufacturer of point-of-care equipment, for example. As an example, it can provide the connection between unstructured text data (for example) entered as annotation data by a user, and the automatic notifications output by one or more analytical devices, in an example. Each prioritization function y can represent a semantic concept such as "charge battery", "analyzer dropped", "memory full."

When automatic notifications are received by the annotation engine 80, the significance engine 96 can identify that a pattern of one or more items of automatic notifications may refer to such a semantic concept and transmit an identifier referring to the semantic concept to the lexical transform engine 98.

The lexical transform engine 98 can contain a data structure, or database, comprising at least one record for each semantic concept. Each record can define one or more words, word fragments, sentences and the like associated with a semantic concept, and likely to be present in associated unstructured comments provided in the annotation data by an analytical device user.

The annotation engine 80 can further comprise a comparison engine 100 configured to receive at least one record from the lexical transform engine and at least one item of annotation data from the annotation data reception unit 92 (optionally categorized by the annotation data categorization unit 93).

The comparison engine 100 can isolate, in the annotation data, one or more items of relevant unstructured or semi-structured text relevant to the semantic concept identified by the lexical analysis engine.

Once isolated, the items of relevant unstructured or semi-structured text may be associated with one or more items of corresponding automatic notification. For example, a logbook entry announcing that "battery is flat" may trigger an identification of one or more characteristic automatic notifications that may be used to infer a condition of the analytical device P1A.

This can enable an analytical device system data record to be generated, in which the relevant unstructured or semi-structured text and associated corresponding automatic notifications can be associated.

Optionally, the analytical device system data record may be output and stored either in the server hosting the data processing agent 40, and/or in an external storage means.

According to an embodiment, the method can further comprise that the correlation can be based on a time relationship between the generation of the one or more automatic notifications and the one or more items of annotation data; or wherein the correlation can be based on one or more correlation rules related to the type of automatic notifications received at the data processing agent.

Figure 9:
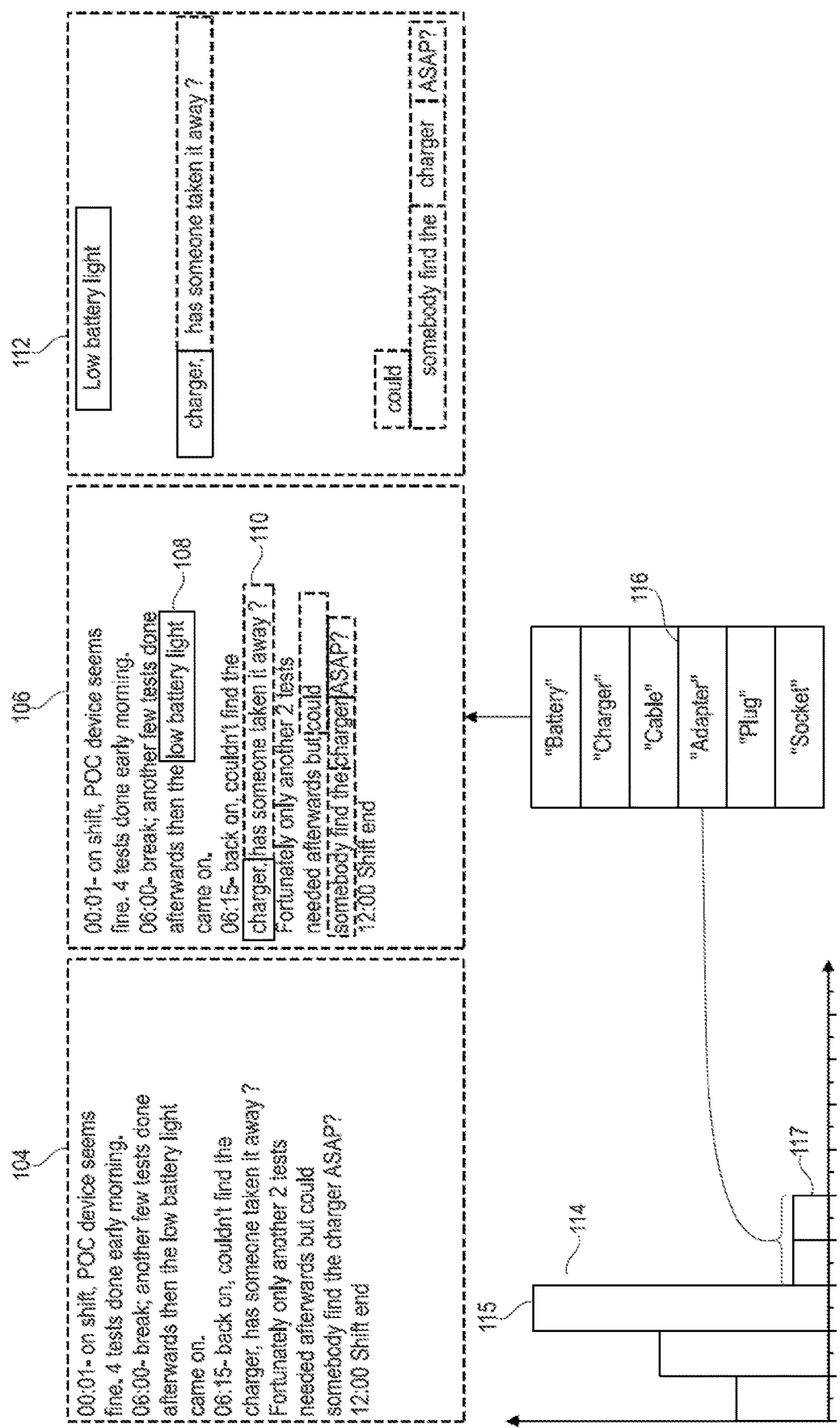
FIG. 9 illustrates schematically an example of correlating automatic notifications with annotation data using a correlation rule set according to an embodiment of the present disclosure.

FIG. 9 schematically illustrates an example of correlating automatic notifications with annotation data using a correlation rule set.

Record 104 can illustrate unformatted unstructured annotation data that may be received, in a non-limiting example, from a text input via a graphical user interface (GUI) on a personal computing device 26.

Histogram 114, as generated by the analysis engine 94, can show a high incidence of automatic notifications of type 115, which in this example can refer to the "motor_PCB" handshake, which it can be preferred to de-emphasize, owing to the large number of messages. On the other hand, analytical device notifications 117 can refer to the "batt_lo_10%" annotation data. It can be preferred to emphasize unstructured annotation data referring to concepts related to power issues.

Accordingly, the significance engine 94 can detect that the "batt_lo_10%" is present, and should be emphasized.

The lexical transform engine 98 can identify that concepts relating to battery and power problems can be identified. A data record 116 in the lexical transform engine 98 can be obtained using the output of the significance engine 94. The data record 116 can provide textual samples of potential entries in unstructured text that can refer to the semantic concept indicated by the automatic notifications.

For example, the textual samples in the data record 116 relating to the "batt_lo_10%" annotation data can comprise the text fragments "battery", "charger", "cable", "adapter", "plug", "socket."

A skilled person can appreciate that completely different textual samples can be provided in data record 116 for other semantic concepts related to the analytical device.

The comparison engine can receive the original unstructured text data 104 and the data record 116 generated by the lexical transform engine. In one example, a text search of each textual sample in the data record 116 can be performed over the unstructured text data 106 of the annotation data.

In a one case, words which are exact and/or close matches to words in the data record 116 can be labelled. For example, the phrase "low battery light" 108 can be labelled because the term "battery" occurs in data record 116.

In another case, the word "charger" can be firstly identified in the unstructured text data 106 of the annotation data and the labelling of the fragment can be extended to encompass the entire clause attached to the word "charger".

As such, it can be possible to identify close matches to text in the data record 116 and/or to extract an entire sentence or clause from the unstructured annotation data within which the text from the data record 116 occurs.

In one example, the output of the annotation engine 90 can be a set of text fragments 112 that can be associated with the analytical device notifications received from one or more analytical devices.

In an example, the output of the annotation engine 90 can be provided directly on a graphical user interface (GUI) as a representation of relevant text fragments from the annotation data.

According to an embodiment, the method can comprise obtaining, at the data processing agent 40, a record from an equipment maintenance database using the notification reporting the condition of the analytical device P1A-P7A, P1B-P7B, wherein the equipment maintenance database can define at least one equipment maintenance action related to the at least one analytical device as a consequence the notification reporting the condition of the analytical device, and generating, at the data processing agent 40, an equipment maintenance notification comprising the at least one equipment maintenance action.

For example, if the data processing agent 40 can infer that the analytical device P1A is within several days of requiring a replacement battery, an appropriate entry in a maintenance schedule may be generated and stored in the equipment maintenance database 75.

Optionally, the maintenance database 75 can comprise individual records 74a, 74b corresponding to individual analytical devices P1A, P2A in the network 10.

Optionally, the individual records 74a, 74b can be generated and/or updated based on the status of the respective model instances P1A(M), P2A(M) referring to the respective analytical devices P1A, P2A.

Optionally, the data processing agent 40 can be configured to generate a custom maintenance schedule for a subset of analytical devices in the network 10, and to display the custom maintenance schedule to a user.

Optionally, the schedule of a maintenance operative may be fused with the maintenance database 75 to enable the selection of maintenance tasks based on the severity of the maintenance condition of a respective analyzer defined by respective model instances P1A(M), P2A(M). For example, a worsening quality control result in analytical device P1A may be prioritized over a routine damage check following a detection, that analyzer P2A was dropped.

According to an embodiment, the method can comprise displaying the condition of the first analytical device P1A-P7A, P1B-P7B to a user via a graphical user interface.

The data processing agent 40 can track the condition of one or more analytical devices P1A-P7A, P1B-P7B in the networks 10A, 10B and, as an example, update corresponding model instances (such as P1A(M)) to reflect a current inferred condition of an analytical device. Therefore, the present state of model instances may be used to derive feedback information for a user.

For example, the data processing agent 40 may generate a message to a user that may be displayed on a user device in the network 10 such as a display 24A of a networked POC-DMS 12A, or smart phone monitoring software 26A. The data processing agent 40 may generate a secure webpage through which the inferred condition of one or more analyzers may be displayed to authenticated users.

For example, the message may be displayed on the interface of an analytical device P1A to which the method refers.

The data processing agent 40 may generate a combined display summarizing the status of all, or a subset, of analytical devices P1A-P7A, P1B-P7B in the networks 10A, 10B.

Optionally, based on data from the maintenance database 75, maintenance tasks may be displayed in a prioritized manner.

Figure 10:
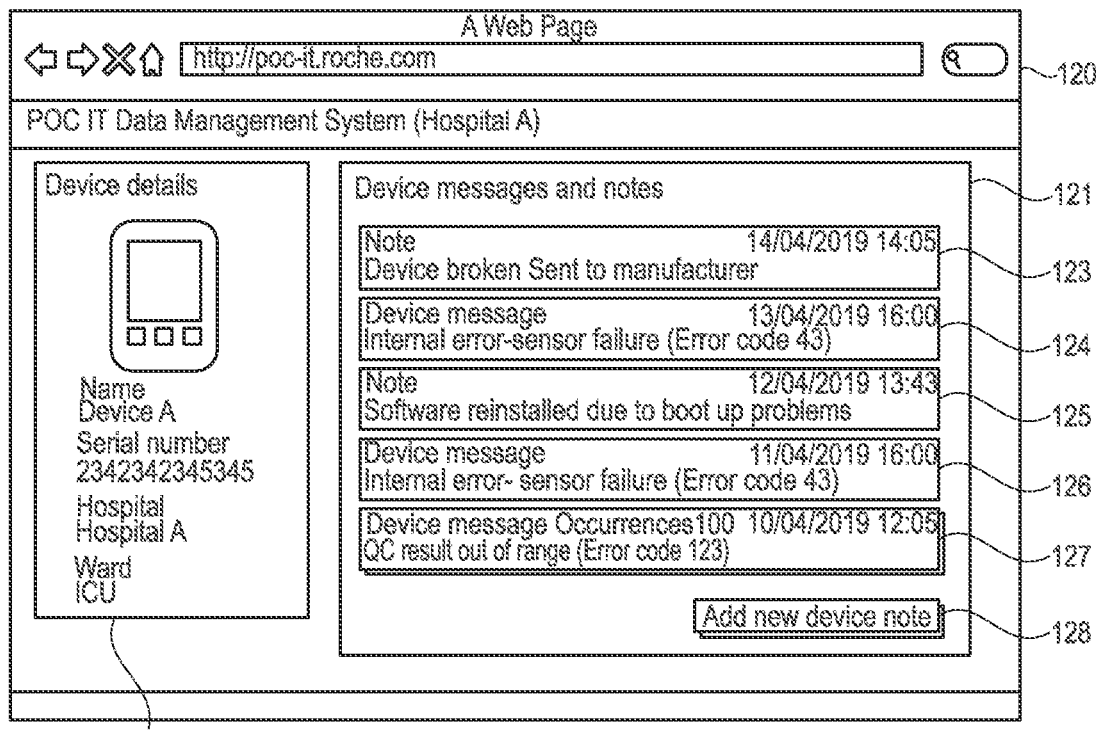
FIG. 10 illustrates schematically an example of a first graphical user interface generated based on a notification reporting the inferred condition of an analytical device in a first hospital according to an embodiment of the present disclosure.

FIG. 10 schematically illustrates an example of a first graphical user interface generated based on a notification reporting the inferred condition of an analytical device in a first hospital ("hospital A" in FIG. 10).

The graphical user interface (GUI) can comprise a browser window 120, which may be displayed in a web browser of, for example, a POC-DMS 12, or a smart phone 26 interface.

Optionally, the browser window can comprise an identification portion 122 enabling identification of the analytical device generated plurality of notifications. The browser window can further comprise a message display portion 121 displaying a plurality of device messages 123-127 generated from automatic notifications sent to a data processing agent 40 by the analytical device "Device A" in hospital A.

Optionally, the browser window 120 can comprise a button 128 enabling a user to append annotation data to one or more of the automatic notifications.

Informally, by reading the history of the messages illustrated in the message display portion 121 in chronological order, it can be clear that 100 quality control failure messages 127 were generated followed by an internal sensor failure 126. The user added annotation data 125 noting that s/he attempted to reinstall software on device A. However, a subsequent sensor failure 124 followed by a final annotation 121 that the device has been sent to a manufacturer can imply that the software reinstall was not the repair device A. The messages and/or notes displayed in message display portion 121 may be input to a model of a data processing agent 40 and used to update the model so that a similar sequence of automatic notifications and annotations at a second network 10B can enable a more accurate diagnosis of the condition of a further device.

Figure 11:
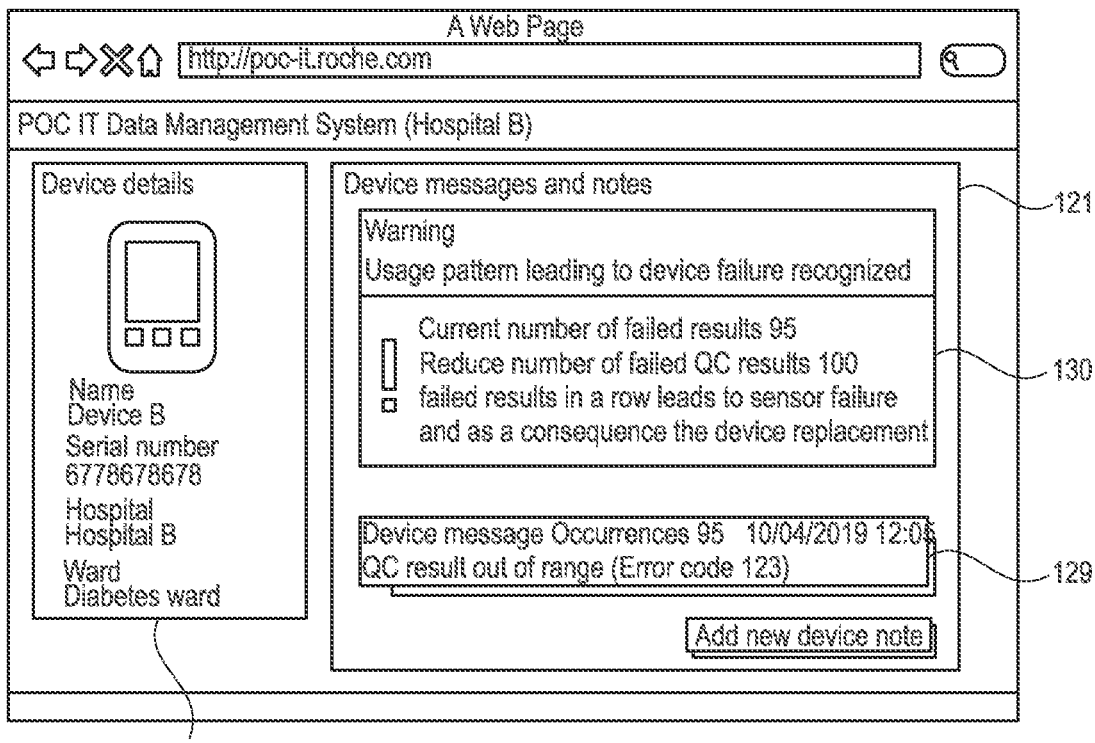
FIG. 11 illustrates schematically an example of a first graphical user interface generated based on a notification reporting the inferred condition of an analytical device in a second hospital according to an embodiment of the present disclosure.

FIG. 11 schematically illustrates an example of a first graphical user interface (GUI) generated based on a notification reporting the inferred condition of an analytical device in a second hospital ("hospital B" in FIG. 11). In other words, a data processing agent 40 can receive a plurality of automatic notifications from device B, an analytical device in the second network 10B.

Using the model of the data processing agent 40 that was trained based on automatic notifications and user annotations received in the first network 10A, the data processing agent 40 can be able to infer that as the number of quality control failures in device B approaches 100, as shown by pop-up box 129, a notification may be generated advising the user of action to be taken in this case, replacing the device B. Therefore, the user may not attempt to reinstall software of device B, as advised by the notification 130.

A skilled person can appreciate that many ways of providing a visual display of the notification reporting the inferred condition may be provided, of which the GUIs illustrated are one option.

An apparatus 39 configured to host a data processing agent 40 for inferring a condition of at least one analytical device P1A-P7A, P1B-P7B based on at least one automatic notification received over a network from the analytical device can be provided. The apparatus 39 can comprise a communications interface 54 and a processor 47 coupled to the communications interface 54 and configured, in operation, to execute the functions of a data processing agent 40 on the processor 47.

The communications interface 54 can be configured to receive at least one automatic notification from at least one analytical device P1A.

The processor 47 can be configured, using the data processing agent 40, to process at least one automatic notification, to thus identify one or more characteristics of the at least one automatic notification from the at least one analytical device P1A.

The processor 47 can be configured to infer, using the data processing agent 40, the condition of the at least one analytical device P1A, by applying the one or more identified characteristics to a model. The processor 47 can be configured to generate, at the data processing agent 40, a notification reporting the inferred condition of the analytical device P1A.

As an example, the apparatus 39 may be a general-purpose server. The apparatus 39 may be a personal computer. An example, the apparatus 39 may be identical to a POC-DMS computer 12 such that the data processing engine can be hosted on a POC-DMS. The apparatus 39 may be an "edge computer".

A system 10A, 10B for analytical device management can be provided. The system can comprise at least one analytical device P1A-P7A, P1B-P7B, an apparatus 39, 23 configured to host a data processing agent 40 for processing data from the apparatus of claim 12 which can be configured to perform the above method, a computing apparatus 12A comprising a user interface 24A, and a network 16A, 16B, 21 configured to communicatively connect the at least one analytical device P1A-P7A, P1B-P7B, the computing device, and the apparatus configured to host the data processing agent 40. The at least one analytical device can be configured to generate at least one notification, and the communication network can be configured to communicate the at least one notification to the data processing agent 40 hosted on the apparatus 39, 23.

Optionally, the data processing agent 40 hosted by the apparatus 39, 23 can be configured to receive a first plurality of automatic notifications from a first set of analytical devices P1A-P7A in a first network 10A. The data processing agent 40 can be configured to train at least one model based on the plurality of automatic notifications from a first set of analytical devices P1A-P7A in a first network 10A. The data processing agent 40 hosted by the apparatus 39, 23 can be configured to receive a second plurality of automatic notifications from a second set of analytical devices P1B-P7B in a second network 10B. The data processing agent can be configured to infer at least one condition of at least one analytical device P1B in the second network using the at least one model trained based on the plurality of automatic notifications from a first set of analytical devices P1A-P7A in the first network 10A. The data processing agent 40 can be configured to generate a notification reporting the inferred condition of at least one analytical device P1B in the second network 10B.

A computer program element comprising computer-readable instructions for controlling an above apparatus, which, when being executed by a processing unit of the apparatus, can be adapted to perform the above method or its embodiments can be provided.

A computer readable medium or signal having stored, or encoded thereon, the above computer program element can be provided.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A computer-implemented method for inferring a condition of an analytical device based on at least one automatic notification received over a network from the analytical device, the computer-implemented method comprising:
receiving, at a data processing agent, the at least one automatic notification from the analytical device;
processing, at the data processing agent, the at least one automatic notification, to identify one or more characteristics of the analytical device;
inferring, at the data processing agent, the condition of the analytical device, by applying the one or more identified characteristics to a model;
receiving, at the data processing agent, at least one item of annotation data via the network;
associating, at the data processing agent, the at least one item of annotation data with the at least one automatic notification;

inferring the condition of the analytical device based, additionally, on the association between the at least one item of annotation data with the at least one automatic notification; and generating, at the data processing agent, a notification reporting the inferred condition of the analytical device.

2. The computer-implemented method according to claim 1, wherein the model at least partially characterizes a type of analytical device used to transmit the at least one automatic notification to the data processing agent.

3. The computer-implemented method according to claim 1, further comprising:
   detecting, at the data processing agent, a connection of a further analytical device to the network;
   identifying, at the data processing agent, if the further analytical device has previously been connected to the network or has not previously been connected to the network; and
   if the further analytical device has previously been connected to the network:
      loading, at the data processing agent, a stored model for use as the model, wherein the stored model characterizes the condition of the further analytical device at an earlier time that it was disconnected from the network,
      processing, at the data processing agent, at least one automatic notification from the further analytical device to identify one or more characteristics of the at least one automatic notification from the analytical device, and
      inferring, at the data processing agent, the condition of the analytical device, by applying the one or more identified characteristics of the at least one automatic notification from the analytical device to the stored model.

4. The computer-implemented method according to claim 1, further comprising:
   detecting, at the data processing agent, a connection of a further analytical device to the network; and
   if the further analytical device has previously not been connected to the network:
      identifying, at the data processing agent, a type of the further analytical device,
      instantiating, at the data processing agent, an additional model for use as the model, wherein the additional model is associated with the identified type of the further analytical device, and
      inferring, at the data processing agent, the condition of the further analytical device, by applying the one or more identified characteristics to the additional model.

5. The computer-implemented method according to claim 1, wherein the model is configured to identify one or more conditions of the analytical device, or their onset, the one or more conditions comprising at least one of: a sensor failure condition, a condition of sensor unreliability, a thermal fault condition, a software or firmware fault condition, a quality control fault condition, a mechanical fault condition, a battery fault condition, a physical shock condition, or a security fault condition.

6. The computer-implemented method according to claim 1, wherein processing, at the data processing agent, the at least one automatic notification to identify one or more characteristics of the analytical device, further comprises:
   receiving, at the data processing agent, a second automatic notification from the analytical device, wherein the at least one automatic notification and the second automatic notification are generated by the analytical device at first and second time points, respectively;
   detecting a time relationship between the at least one automatic notification and the second automatic notification based on the first and second time points; and
   identifying the one or more characteristics based at least on the detected time relationship, and optionally on at least one of a type of the at least one automatic notification, a type of the second automatic notification, or a type of the analytical device from which the at least one automatic notification and the second automatic notification originated.

7. The computer-implemented method according to claim 1, wherein the analytical device is configured to analyze biological samples to identify a biomarker of a medical condition.

8. The computer-implemented method according to claim 1, wherein the model is one of, or a combination of, a rules-based model, a linear regression, a decision tree, a support vector machine, a k-nearest neighbor model, a random forest model, an auto encoder, a convolutional neural network, a recursive neural network, a deep belief network, or a transfer learning model.

9. The computer-implemented method according to claim 1, further comprising displaying the condition of the analytical device to a user via a graphical user interface.

10. The computer-implemented method according to claim 1, further comprising:
    obtaining, at the data processing agent, a record from an equipment maintenance database using the notification reporting the inferred condition of the analytical device, wherein the equipment maintenance database defines at least one equipment maintenance action related to the analytical device as a consequence the notification reporting the inferred condition of the analytical device; and
    generating, at the data processing agent, an equipment maintenance notification comprising the at least one equipment maintenance action.

11. An apparatus configured to host a data processing agent for inferring a condition of an analytical device based on at least one automatic notification received over a network from the analytical device, the apparatus comprising:
    a communications interface; and
    a processor coupled to the communications interface and configured, in operation, to execute functions of a data processing agent on the processor, wherein the communications interface is configured to receive, at a data processing agent, the at least one automatic notification from the analytical device, wherein the processor is configured, using the data processing agent, to process the at least one automatic notification, to identify one or more characteristics of the analytical device based on the at least one automatic notification from the analytical device, wherein the processor is configured to infer, using the data processing agent, the condition of the analytical device, by applying the one or more identified characteristics to a model, and wherein the processor is further configured to:
       receive, at the data processing agent, at least one item of annotation data via the network;
       associate, at the data processing agent, the at least one item of annotation data with the at least one automatic notification;
       infer the condition of the analytical device based, additionally, on the association between the at least one item of annotation data with the at least one automatic notification; and generate, at the data processing agent, a notification reporting the inferred condition of the analytical device.

12. A system for analytical device management, the system comprising:

at least one analytical device;

an apparatus configured to host a data processing agent for processing data from the apparatus of claim 11 which is configured to perform the computer-implemented method of claim 1;

a computing apparatus comprising a user interface; and a communication network configured to communicatively connect the at least one analytical device, the computing device, and the apparatus configured to host the data processing agent, wherein the at least one analytical device is configured to generate at least one notification, and the communication network is configured to communicate at least one notification to the data processing agent hosted on the apparatus.

13. A computer program element comprising computer-readable instructions for controlling an apparatus according to claim 11 which, when being executed by a processing unit of the apparatus, is adapted to perform the computer-implemented method of claim 1.

14. A non-transitory computer readable medium or signal having stored, or encoded thereon, the computer program element of claim 13.

* * * * *